US008209745B2

(12) United States Patent
Huber et al.

(10) Patent No.: US 8,209,745 B2
(45) Date of Patent: Jun. 26, 2012

(54) AUTOMATIC POPULATION OF AN ACCESS CONTROL LIST TO MANAGE FEMTO CELL COVERAGE

(75) Inventors: Kurt Donald Huber, Kennesaw, GA (US); Judson John Flynn, Decatur, GA (US); William Gordon Mansfield, Sugar Hill, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 858 days.

(21) Appl. No.: 12/275,996

(22) Filed: Nov. 21, 2008

(65) Prior Publication Data

US 2009/0288152 A1 Nov. 19, 2009

Related U.S. Application Data

(60) Provisional application No. 61/052,813, filed on May 13, 2008.

(51) Int. Cl.
*H04L 29/06* (2006.01)
(52) U.S. Cl. ............................................. 726/6; 713/182
(58) Field of Classification Search ........ 726/6; 713/182
See application file for complete search history.

(56) References Cited

U.S. PATENT DOCUMENTS

| | | | |
|---|---|---|---|
| 5,745,559 A * | 4/1998 | Weir ............................. | 379/199 |
| 5,864,764 A | 1/1999 | Thro et al. | |
| 6,052,594 A | 4/2000 | Chuang et al. | |
| 6,151,505 A | 11/2000 | Larkins | |
| 6,219,786 B1 | 4/2001 | Cunningham et al. | |
| 6,266,537 B1 | 7/2001 | Kashitani et al. | |
| 6,363,261 B1 | 3/2002 | Raghavan | |
| 6,483,852 B1 | 11/2002 | Jacquet et al. | |
| 6,484,096 B2 | 11/2002 | Wong | |
| 6,710,651 B2 | 3/2004 | Forrester | |
| 6,718,023 B1 | 4/2004 | Zolotov | |
| 7,080,139 B1 | 7/2006 | Briggs et al. | |
| 7,142,861 B2 | 11/2006 | Murai | |
| 7,146,153 B2 | 12/2006 | Russell | |
| 7,209,739 B1 | 4/2007 | Narayanabhatla | |

(Continued)

FOREIGN PATENT DOCUMENTS

GB 2425921 A 11/2006

OTHER PUBLICATIONS

OA dated Aug. 18, 2011 for U.S. Appl. No. 12/275,416, 39 pages.

(Continued)

*Primary Examiner* — Michael Pyzocha
(74) *Attorney, Agent, or Firm* — Turocy & Watson, LLP

(57) ABSTRACT

System(s) and method(s) provide access management to femto cell service through access control list(s) (e.g., white list(s)). White list(s) includes a set of subscriber station(s) identifier numbers, codes, or tokens, and also can include additional fields for femto cell access management based on desired complexity. White list(s) can have associated white list profile(s) therewith to establish logic of femto coverage access based on the white list(s). Various example aspects such as white list(s) management, maintenance and dissemination; automatic population or pre-configuration; and inclusion of wireless device(s) or subscriber(s) are also provided. A component can implement automatic population of white list fields based at least in part on a set of received identifiers. In addition, autonomously determined identifiers can be employed to populate a white list. Identifier(s) available for automatic population are validated prior to inclusion in a white list, to ensure the identifier(s) are allowed for inclusion therein.

22 Claims, 17 Drawing Sheets

U.S. PATENT DOCUMENTS

| | | | |
|---|---|---|---|
| 7,277,410 B2 | 10/2007 | Horneman | |
| 7,317,931 B2 | 1/2008 | Guo | |
| 7,370,356 B1 * | 5/2008 | Guo | 726/22 |
| 7,496,383 B2 | 2/2009 | Kurata | |
| 7,516,219 B2 | 4/2009 | Moghaddam et al. | |
| 7,613,444 B2 | 11/2009 | Lindqvist et al. | |
| 7,623,857 B1 | 11/2009 | O'Neil et al. | |
| 7,633,910 B2 | 12/2009 | Zhun et al. | |
| 7,751,826 B2 | 7/2010 | Gardner | |
| 7,768,983 B2 | 8/2010 | Nylander et al. | |
| 7,885,644 B2 | 2/2011 | Gallagher et al. | |
| 7,929,537 B2 | 4/2011 | Vasudevan et al. | |
| 7,929,970 B1 | 4/2011 | Gunasekara | |
| 7,941,144 B2 | 5/2011 | Nylander et al. | |
| 7,995,994 B2 | 8/2011 | Khetawat et al. | |
| 8,108,923 B1 * | 1/2012 | Satish et al. | 726/11 |
| 2002/0098837 A1 | 7/2002 | Ferrario et al. | |
| 2002/0123365 A1 | 9/2002 | Thorson | |
| 2002/0142791 A1 | 10/2002 | Chen et al. | |
| 2003/0109271 A1 | 6/2003 | Lewis et al. | |
| 2003/0125044 A1 | 7/2003 | Deloach | |
| 2003/0142637 A1 | 7/2003 | Khawer et al. | |
| 2003/0153302 A1 | 8/2003 | Lewis et al. | |
| 2004/0111382 A1 | 6/2004 | Haji-Ioannou | |
| 2004/0125781 A1 | 7/2004 | Walter et al. | |
| 2004/0236702 A1 * | 11/2004 | Fink et al. | 705/73 |
| 2004/0258003 A1 | 12/2004 | Kotot et al. | |
| 2005/0003797 A1 | 1/2005 | Baldwin | |
| 2005/0009499 A1 | 1/2005 | Koster | |
| 2005/0026650 A1 | 2/2005 | Russell | |
| 2005/0075114 A1 | 4/2005 | Dennison et al. | |
| 2005/0108529 A1 * | 5/2005 | Juneau | 713/168 |
| 2005/0144279 A1 * | 6/2005 | Wexelblat | 709/225 |
| 2005/0160276 A1 | 7/2005 | Braun et al. | |
| 2005/0172148 A1 | 8/2005 | Ying | |
| 2005/0177645 A1 | 8/2005 | Dowling et al. | |
| 2005/0223389 A1 * | 10/2005 | Klein et al. | 719/321 |
| 2005/0250527 A1 | 11/2005 | Jugl | |
| 2005/0254451 A1 | 11/2005 | Grosbach | |
| 2006/0031387 A1 | 2/2006 | Hamzeh et al. | |
| 2006/0031493 A1 * | 2/2006 | Cugi | 709/225 |
| 2006/0046647 A1 | 3/2006 | Parikh et al. | |
| 2006/0075098 A1 | 4/2006 | Becker et al. | |
| 2006/0223498 A1 | 10/2006 | Gallagher et al. | |
| 2006/0281457 A1 * | 12/2006 | Huotari et al. | 455/435.1 |
| 2007/0002844 A1 | 1/2007 | Ali | |
| 2007/0008894 A1 | 1/2007 | Lynch et al. | |
| 2007/0025245 A1 * | 2/2007 | Porras et al. | 370/229 |
| 2007/0032225 A1 | 2/2007 | Konicek et al. | |
| 2007/0032269 A1 | 2/2007 | Shostak | |
| 2007/0074272 A1 | 3/2007 | Watanabe | |
| 2007/0097938 A1 | 5/2007 | Nylander et al. | |
| 2007/0097939 A1 | 5/2007 | Nylander et al. | |
| 2007/0097983 A1 | 5/2007 | Nylander et al. | |
| 2007/0099561 A1 | 5/2007 | Voss | |
| 2007/0124802 A1 | 5/2007 | Anton et al. | |
| 2007/0155421 A1 | 7/2007 | Alberth et al. | |
| 2007/0167175 A1 | 7/2007 | Wong | |
| 2007/0183427 A1 * | 8/2007 | Nylander et al. | 370/395.2 |
| 2007/0184815 A1 | 8/2007 | Aebi | |
| 2007/0199076 A1 | 8/2007 | Rensin et al. | |
| 2007/0258418 A1 | 11/2007 | Wurtenberger et al. | |
| 2007/0270152 A1 | 11/2007 | Nylander et al. | |
| 2007/0275739 A1 * | 11/2007 | Blackburn | 455/466 |
| 2007/0287501 A1 | 12/2007 | Hoshina | |
| 2008/0043972 A1 * | 2/2008 | Ruetschi et al. | 379/216.01 |
| 2008/0049702 A1 | 2/2008 | Meylan et al. | |
| 2008/0065752 A1 * | 3/2008 | Ch'ng et al. | 709/223 |
| 2008/0076392 A1 | 3/2008 | Khetawat et al. | |
| 2008/0076393 A1 | 3/2008 | Khetawat et al. | |
| 2008/0076398 A1 * | 3/2008 | Mate et al. | 455/414.2 |
| 2008/0076412 A1 | 3/2008 | Khetawat et al. | |
| 2008/0076419 A1 | 3/2008 | Khetawat et al. | |
| 2008/0076420 A1 | 3/2008 | Khetawat et al. | |
| 2008/0076425 A1 | 3/2008 | Khetawat et al. | |
| 2008/0081636 A1 | 4/2008 | Nylander et al. | |
| 2008/0082538 A1 * | 4/2008 | Meijer et al. | 707/9 |
| 2008/0126531 A1 * | 5/2008 | Setia et al. | 709/224 |
| 2008/0132239 A1 | 6/2008 | Khetawat et al. | |
| 2008/0133742 A1 | 6/2008 | Southiere et al. | |
| 2008/0151807 A1 | 6/2008 | Meier et al. | |
| 2008/0168099 A1 | 7/2008 | Skaf | |
| 2008/0181184 A1 | 7/2008 | Kezys | |
| 2008/0207170 A1 | 8/2008 | Khetawat et al. | |
| 2008/0242280 A1 | 10/2008 | Shapiro et al. | |
| 2008/0244148 A1 | 10/2008 | Nix et al. | |
| 2008/0254792 A1 | 10/2008 | Ch'ng | |
| 2008/0281687 A1 | 11/2008 | Hurwitz et al. | |
| 2008/0282327 A1 | 11/2008 | Winget et al. | |
| 2008/0299984 A1 | 12/2008 | Shimomura | |
| 2008/0299992 A1 | 12/2008 | Eitan et al. | |
| 2008/0305801 A1 * | 12/2008 | Burgess et al. | 455/444 |
| 2008/0318551 A1 | 12/2008 | Palamara et al. | |
| 2009/0037973 A1 | 2/2009 | Gustave et al. | |
| 2009/0046665 A1 | 2/2009 | Robson et al. | |
| 2009/0047945 A1 | 2/2009 | Zhang | |
| 2009/0061821 A1 | 3/2009 | Chen et al. | |
| 2009/0061873 A1 * | 3/2009 | Bao et al. | 455/436 |
| 2009/0082010 A1 | 3/2009 | Lee | |
| 2009/0082020 A1 * | 3/2009 | Ch'ng et al. | 455/435.3 |
| 2009/0092096 A1 | 4/2009 | Czaja | |
| 2009/0092097 A1 * | 4/2009 | Nylander et al. | 370/331 |
| 2009/0093232 A1 | 4/2009 | Gupta et al. | |
| 2009/0094351 A1 | 4/2009 | Gupta et al. | |
| 2009/0094680 A1 | 4/2009 | Gupta et al. | |
| 2009/0097436 A1 * | 4/2009 | Vasudevan et al. | 370/328 |
| 2009/0111499 A1 | 4/2009 | Bosch | |
| 2009/0122773 A1 | 5/2009 | Gogic | |
| 2009/0124262 A1 | 5/2009 | Vela et al. | |
| 2009/0131050 A1 | 5/2009 | Osborn | |
| 2009/0135749 A1 | 5/2009 | Yang | |
| 2009/0135794 A1 | 5/2009 | Su et al. | |
| 2009/0156213 A1 | 6/2009 | Spinelli et al. | |
| 2009/0163216 A1 * | 6/2009 | Hoang et al. | 455/450 |
| 2009/0163224 A1 | 6/2009 | Dean | |
| 2009/0164547 A1 * | 6/2009 | Ch'ng et al. | 709/201 |
| 2009/0170440 A1 * | 7/2009 | Eyuboglu et al. | 455/63.3 |
| 2009/0170528 A1 | 7/2009 | Bull et al. | |
| 2009/0191844 A1 | 7/2009 | Morgan et al. | |
| 2009/0191845 A1 * | 7/2009 | Morgan et al. | 455/411 |
| 2009/0210324 A1 | 8/2009 | Bhogal | |
| 2009/0215452 A1 * | 8/2009 | Balasubramanian et al. | 455/434 |
| 2009/0221303 A1 | 9/2009 | Soliman | |
| 2009/0233574 A1 | 9/2009 | Shinozaki | |
| 2009/0245176 A1 * | 10/2009 | Balasubramanian et al. | 370/328 |
| 2009/0253421 A1 | 10/2009 | Camp et al. | |
| 2009/0253432 A1 * | 10/2009 | Willey et al. | 455/435.2 |
| 2009/0279701 A1 | 11/2009 | Moisand et al. | |
| 2009/0291667 A1 | 11/2009 | Vakil et al. | |
| 2010/0022266 A1 | 1/2010 | Villier | |
| 2010/0040026 A1 | 2/2010 | Melkesetian | |
| 2010/0260068 A1 * | 10/2010 | Bhatt et al. | 370/254 |
| 2011/0200022 A1 * | 8/2011 | Annamalai | 370/338 |

OTHER PUBLICATIONS

OA dated Sep. 14, 2011 for U.S. Appl. No. 12/276,002, 35 pages.
OA dated Oct. 5, 2011 for U.S. Appl. No. 12/276,058, 37 pages.
OA dated Oct. 6, 2011 for U.S. Appl. No. 12/465,483, 50 pages.
OA dated Oct. 4, 2011 for U.S. Appl. No. 12/484,135, 44 pages.
OA dated Jul. 21, 2011 for U.S. Appl. No. 12/175,293, 30 pages.
International Search Report and Written Opinion dated Oct. 27, 2009 for PCT Application Serial No. PCT/US2009/043861, 14 Pages.
International Search Report and Written Opinion mailed Feb. 23, 2010, for PCT Application No. PCT/US2009/043846, 13 pages.
OA dated Dec. 31, 2009 for U.S. Appl. No. 11,457,129, 16 pages.
OA dated Apr. 17, 2009 for U.S. Appl. No. 11/276,269, 15 pages.
OA dated Nov. 4, 2008 for U.S. Appl. No. 11/276,269, 15 pages.
OA dated Mar. 29, 2011 for U.S. Appl. No. 12/276,002, 37 pages.
OA dated Apr. 13, 2011 for U.S. Appl. No. 12/276,058, 40 pages.
OA dated Apr. 19, 2011 for U.S. Appl. No. 12/276,238, 22 pages.
OA dated May 5, 2011 for U.S. Appl. No. 12/275,015, 32 pages.
OA dated Jun. 14, 2011 for U.S. Appl. No. 12/275,878, 35 pages.
OA dated Jun. 22, 2011 for U.S. Appl. No. 12/484,072, 38 pages.
OA dated Jul. 7, 2011 for U.S. Appl. No. 12/276,257, 24 pages.
OA dated Jun. 28, 2011 for U.S. Appl. No. 12/275,925, 18 pages.

OA dated Jun. 8, 2011 for U.S. Appl. No. 12/484,026, 30 pages.
OA dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
OA dated Oct. 24, 2011 for U.S. Appl. No. 12/275,925, 14 pages.
OA dated Nov. 30, 2011 for U.S. Appl. No. 12/275,878, 38 pages.
OA dated Jan. 5, 2012 for U.S. Appl. No. 12/465,585, 43 pages.
OA dated Oct. 25, 2011 for U.S. Appl. No. 12/465,580, 39 pages.
OA dated Nov. 8, 2011 for U.S. Appl. No. 12/465,468, 50 pages.
OA dated Dec. 28, 2011 for U.S. Appl. No. 12/175,293, 38 pages.
OA dated Nov. 21, 2011 for U.S. Appl. No. 12/484,026, 37 pages.
OA dated Dec. 14, 2011 for U.S. Appl. No. 12/484,072, 44 pages.
OA dated Nov. 1, 2011 for U.S. Appl. No. 12/816,087, 33 pages.
OA dated Mar. 30, 2012 for U.S. Appl. No. 12/484,026, 30 pages.
OA dated Mar. 5, 2012 for U.S. Appl. No. 12/465,598, 55 pages.
OA dated Mar. 19, 2012 for U.S. Appl. No. 12/276,120, 68 pages.

* cited by examiner

AUTOMATIC POPULATION OF AN ACCESS CONTROL LIST TO MANAGE FEMTO CELL COVERAGE

CROSS-REFERENCE TO RELATED APPLICATION

This application claims the benefit of U.S. Provisional Patent application Ser. No. 61/052,813 entitled "MANAGEMENT OF ACCESS TO FEMTO CELL COVERAGE" and filed on May 13, 2008. The entirety of the above-referenced application is incorporated by reference herein.

TECHNICAL FIELD

The subject innovation relates to wireless communications and, more particularly, to management of access to femto cell coverage by a subscriber and subscriber stations.

BACKGROUND

Femto cells—building-based wireless access points interfaced with a wired broadband network—are generally deployed to improve indoor wireless coverage provided by a wireless network operator. Femto cells typically operate in licensed portions of the electromagnetic spectrum, and generally offer plug-and-play installation; e.g., automatic configuration of femto access point. Improved indoor coverage includes stronger signal and improved reception (e.g., voice or sound), ease of session or call initiation and session or call retention as well. Coverage of a femto cell, or femto AP, is intended to be confined within the bounds of an indoor compound, in order to mitigate interference among mobile stations covered by a macro cell and terminals covered by the femto AP. Additionally, confined coverage can reduce cross-talk among terminals serviced by disparate, neighboring femto cells as well.

Coverage improvements via femto cells can also mitigate customer attrition as long as a favorable subscriber perception regarding voice coverage and other data services with substantive delay sensitivity is attained. A positive customer experience can depend on adequate access management to femto cell service. Such adequate access management can include configuration procedures of a provisioned femto cell access point deployed in a coverage area. Thus, cumbersome configuration procedures that involve interaction with customer service representatives, fail to provide versatility with substantially low complexity, or are not directed to a broad spectrum of consumers with various disparate degrees of technological savvy, can hinder femto cell service adoption and thus prevent pervasive dissemination of utilization of home-based and business-based femto access points and exploitation of operational efficiencies thereof.

SUMMARY

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The subject innovation provides system(s) and method(s) to manage access to femto cell service through access control list(s), e.g., white list(s). Such white list(s) can be configured via a networked interface which facilitates access management to a femto cell. White list(s) includes a set of subscriber station(s) identifier numbers, codes or tokens, and can also include additional fields that can contain information respectively associated with communication devices to facilitate femto cell access management based at least in part on desired complexity; for instance, an additional field in a white list can be a logic parameter that determines whether an associated identifier is available for dissemination across disparate white lists. Various illustrative aspects such as white list(s) management, maintenance and dissemination; automatic population or pre-configuration; and inclusion of wireless device(s) or subscriber(s) are also provided.

In an aspect of the subject innovation, a component can implement automatic population of white list fields based at least in part on a set of received identifiers for mobile stations. Such identifiers can be received through an interface component in a point of sales platform, as part of provisioning of a femto access point. Subscriber can be prompted to provide identifiers and coverage parameters that determine access privileges intended for wireless devices respectively associated with provided identifiers. Alternatively, or in addition, such identifiers can be received through a networked interface component (e.g., an online portal for femto access point management) as a part of a configuration procedure of a femto access point to which the white list, or access control list, is directed to. In addition, autonomously determined identifiers (e.g., a mobile subscriber integrated services digital network number (MSISDN)) can be employed to populate a white list. Autonomous determination can be based at least in part on an extracted pattern of call activity for a consumer that acquires or provisions a femto access point. A component that provides for management of white list(s) can validate received identifier(s) available for automatic population prior to inclusion in a white list, to ensure the identifier(s) are allowed for inclusion therein, and to ensure security and privacy aspects of disparate subscribers are observed.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention may be employed. Other aspects, advantages and novel features of the invention will become apparent from the following detailed description of the invention when considered in conjunction with the drawings.

DETAILED DESCRIPTION

Figure 1:
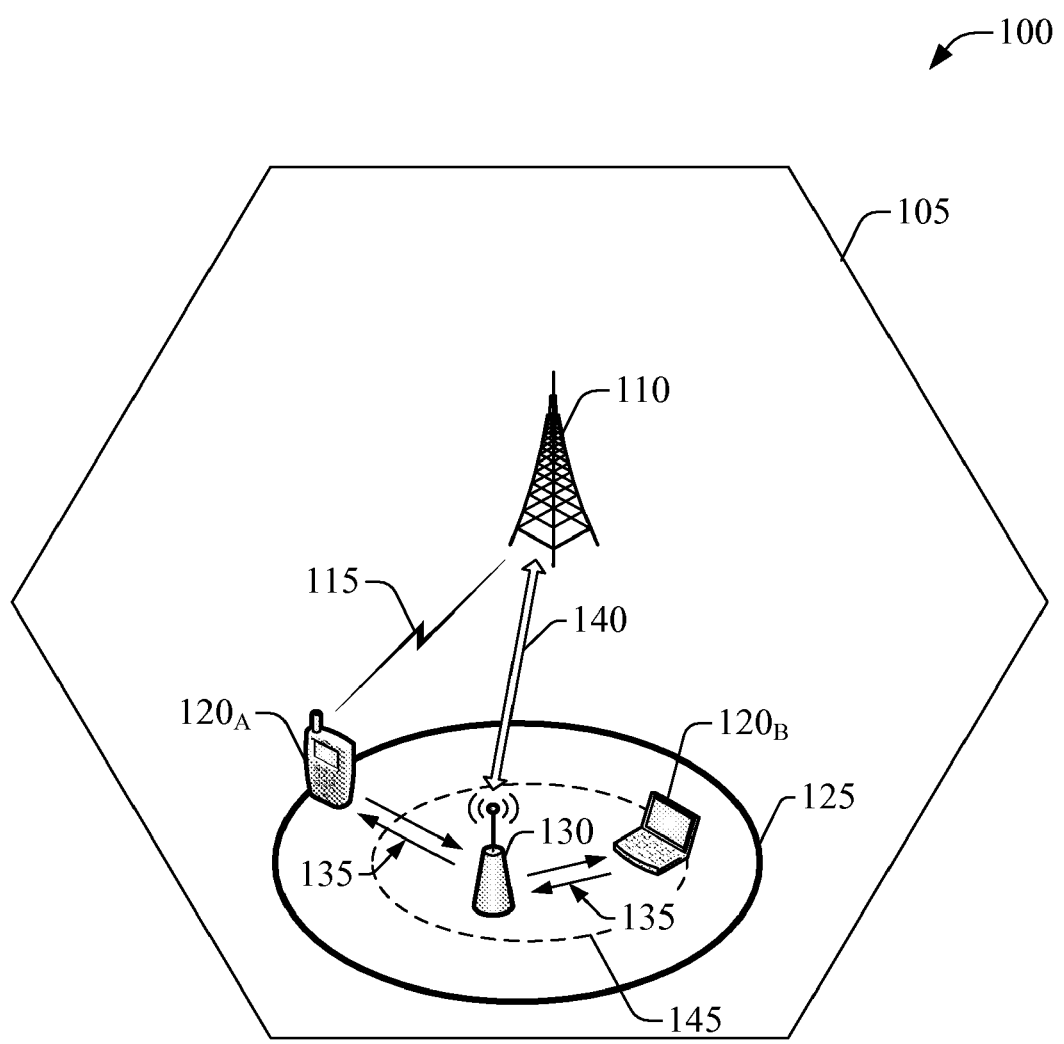
FIG. 1 a schematic deployment of a macro cell and a femto cell for wireless coverage in accordance with aspects described herein.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component," "system," "platform," and the like are intended to refer to a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," subscriber station," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B," "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

Furthermore, the terms "user," "subscriber," "customer," "consumer," "prosumer," "agent," and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms) which can provide simulated vision, sound recognition and so forth. As utilized herein, the term "prosumer" indicate the following contractions: professional-consumer and producer-consumer.

Referring to the drawings, FIG. 1 illustrates a schematic wireless environment (e.g., a network) 100 in which a femto cell can exploits various aspects described in the subject specification. In wireless environment 100, area 105 represents a coverage macro cell which is served by base station 110. Macro coverage is generally intended for outdoors locations for servicing mobile wireless devices, like UE $120_A$, and such coverage is achieved via a wireless link 115. In an aspect, UE 120 can be a 3rd Generation Partnership Project (3GPP) Universal Mobile Telecommunication System (UMTS) mobile phone.

Within macro coverage cell 105, a femto cell 145, served by a femto access point 130, can be deployed. A femto cell typically covers an area 125 that is determined, at least in part, by transmission power allocated to femto AP 130, path loss, shadowing, and so forth. Coverage area typically is spanned by a coverage radius that ranges from 20 to 50 meters. Confined coverage area 145 is generally associated with an indoors area, or a building, which can span about 5000 sq. ft. Generally, femto AP 130 typically services a few (e.g., 1-9) wireless devices (e.g., subscriber station $120_B$) within confined coverage area 145. In an aspect, femto AP 130 can integrate seamlessly with substantially any packet switched (PS)-based and circuit switched (CS)-based network; for instance, femto AP 130 can integrate into an existing 3GPP Core via conventional interfaces like Iu-CS, Iu-PS, Gi, Gn. In another aspect, femto AP 130 can exploit high-speed downlink packet access in order to accomplish substantive bitrates. In yet another aspect, femto AP 130 has a LAC (location area code) and RAC (routing area code) that is different than the underlying macro network. These LAC and RAC are used to identify subscriber station location for a variety of reasons, most notably to direct incoming voice and data traffic to appropriate paging transmitters.

As a subscriber station, e.g., UE $120_A$, leaves macro coverage (e.g., cell 105) and enters femto coverage (e.g., area 125), as illustrated in environment 100, UE $120_A$ attempts to attach to the femto AP 130 through transmission and reception of attachment signaling, effected via a FL/RL 135; in an aspect, the attachment signaling can include a Location Area Update (LAU) and/or Routing Area Update (RAU). Attachment attempts are a part of procedures to ensure mobility, so voice calls and sessions can continue even after a macro-to-femto transition or vice versa. It is to be noted that UE 120 can be employed seamlessly after either of the foregoing transitions. Femto networks are also designed to serve stationary or slow-moving traffic with reduced signaling loads compared to macro networks. A femto service provider (e.g., an entity that commercializes, deploys, and/or utilizes femto access point 130) is therefore inclined to minimize unnecessary LAU/RAU signaling activity at substantially any opportunity to do so, and through substantially any available means. It is to be noted that substantially any mitigation of unnecessary attachment signaling/control is advantageous for femto cell operation. Conversely, if not successful, UE 120 is generally commanded (through a variety of communication means) to select another LAC/RAC or enter "emergency calls only" mode. It is to be appreciated that this attempt and handling process can occupy significant UE battery, and femto AP capacity and signaling resources as well.

When an attachment attempt is successful, UE 120 is allowed on femto cell 125 and incoming voice and data traffic are paged and routed to the subscriber through the femto AP 130. It is to be noted also that data traffic is typically routed through a backhaul broadband wired network backbone 140 (e.g., optical fiber backbone, twisted-pair line, T1/E1 phone line, digital subscriber line (DSL), or coaxial cable). To this end, femto AP 130 is connected to the broadband backhaul network backbone 140 via a broadband modem (not shown).

It is to be noted that as a femto AP 130 generally relies on a backhaul network backbone 140 for routing and paging, and for packet communication, substantially any quality of service (QoS) can be handled for heterogeneous packetized traffic. Namely, packet flows established for wireless devices (like terminals $120_A$ and $120_B$) served by femto AP 130, and for devices served through the backhaul network pipe 140. It is to be noted that to ensure a positive subscriber experience, or perception, it is important for femto AP 130 to maintain a high level of throughput for traffic (e.g., voice and data) utilized on a mobile device for one or more subscribers while in the presence of external, additional packetized, or broadband, traffic associated with applications (web browsing, data transfer (e.g., content upload), and the like) executed in devices within the femto coverage area (e.g., either area 125 or area 145).

Figure 2:
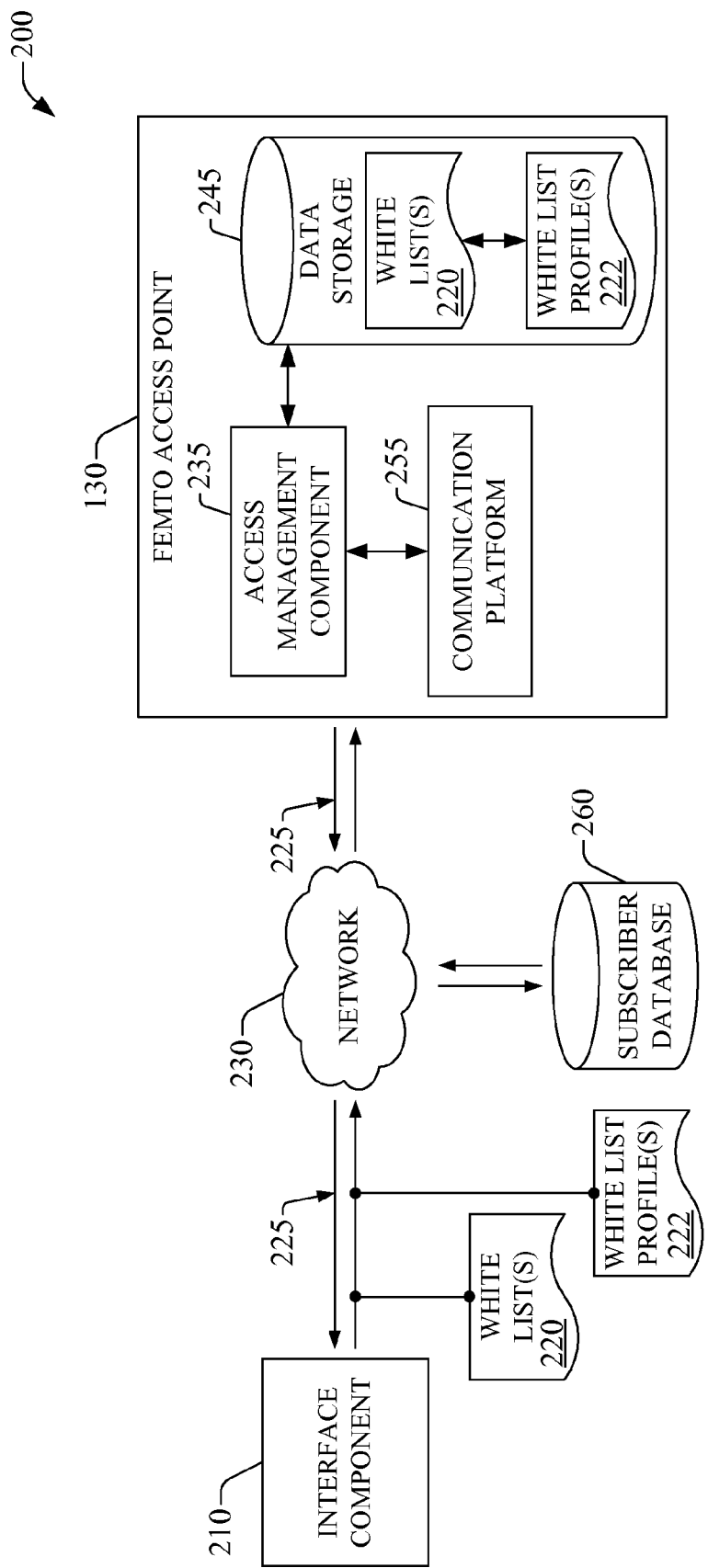
FIG. 2 is a block diagram of an example system that facilitates selection of subscribers, and mobile devices linked thereto, to access coverage from a femto cell in accordance with aspects disclosed herein.

FIG. 2 is a block diagram of an example system 200 that facilitates selection of subscribers, and mobile devices linked thereto, to access coverage from a femto cell; selection can enable or disable coverage for specific subscriber(s) or subscriber station(s). Means provided by example system 200 to authorize, permanently or temporarily, or revoke access to specific subscribers, or subscriber station(s), comprise what is herein termed as a "White List(s)" (e.g., access control list(s))—an instrument for management of access to femto cell coverage.

In example system 200, an interface component 210 facilitates configuration, or set up, of a list (e.g., white list 220) of wireless mobile station numbers approved for coverage through femto access point 130. It is to be noted that substantially any identification token(s), label(s), or code(s) that identify a subscriber station can be employed. In addition, a white list profile(s) 222 associated with white list(s) 220 can also be configured through system interface component 210, wherein white list profile(s) 222 applies logic and parameters that control, or manage, content in associated white list(s), such as subscriber station numbers (e.g., MSISDNs), codes or tokens. In an aspect, white list profile(s) 222 parameters that control utilization logic of white list(s) content include, without being limited to: (i) temporary access control, e.g., full access for a specific time interval such as days or hours; (ii) access type control, which can determine access only within a window of time in a day (voice and data allowed from 9:00 a-6:00 p, or voice allowed after 9:00 p which can facilitate billing schemes already established by an operator/service provider); or (iii) access to specific applications or services such as scheduler, calendar(s), news streaming, authoring tools, gaming, video and music, etc. It should be appreciated that parameters in white list profile(s) 222 establish femto service or coverage privileges for subscriber station(s) identified and recorded in white list(s) 220.

Interface 210 is networked (e.g., via a wide area network (WAN), local area network (LAN), or backhaul pipe like backhaul network backbone 140) with femto AP 130 and conveys white list(s) 220 and white list profile(s) 222 over network link(s) 225. In an aspect, interface component 210 can be a web-based, online graphic user interface (GUI); however, other networked interfaces that facilitate to enter, or configure, white list(s) are possible; for instance, voice or sound commanded interface(s), touch commanded interface(s), biometric commanded interfaces(s), and the like. A communication platform 255 facilitates reception of the white list(s) 220 and conveys white list(s) 220 to an access management component 235 that can exploit the white list(s) 220 to manage access to coverage provided by femto AP 130. White list(s) 220 and white list profile(s) 222 can be stored in the data storage 245 in the femto AP 130; even though white list(s) 220 and white list profile(s) 222 can be stored in disparate network components like a network component administered by a service operator. In addition, interface component 210 can access a subscriber database 260 through network 230, in order to extract identification numbers or identifiers, codes, tokens, or labels for subscribers/subscriber stations that can be entered in a white list (e.g., white list(s) 220).

In an illustrative, non-limiting aspect of the innovation, white list(s) 220 (or any set of numbers, codes or tokens thereon) that comprise a set of mobile phones or mobile devices approved for coverage by femto AP 130 can be portable through accounts or billing groups associated with a set of subscribers to a service operator that administers femto AP 130, or a macro network. As an illustration, white list(s) 220 can support up to N fields (N a positive integer; e.g., N=50) for unique mobile phone numbers (e.g., MSIDSNs), or any suitable identifying codes or tokens. The number N of fields can be determined, or configured, by a service operator based at least in part on technical aspects (like network resources, quality of service consideration, macro area of coverage (e.g., MSA/RSA), and so on) and commercial aspects (such as promotional considerations, mitigation of customer attrition, gains in market share, etc.) of provision of coverage. As an example, N can be subscriber dependent or femto AP dependent; e.g., premium subscriber that consume substantive volume of data, like prosumers, can have larger N than subscribers that primarily consume voice. It should be appreciated that the magnitude of N can also be determined dynamically, and augmented on a subscriber-need basis within bounds determined by network capacity.

In contrast to management of access authorization via femto access point 130, it should be appreciated that configuration of white list(s) 220 (registration authorization for femto coverage) and white list profile(s) 222 through network mechanisms (e.g., interface component 210) provides at least the following advantages. It is to be noted that the following advantages are illustrative and not limiting, as other advantages associated with white list(s) 220 are possible and are intended to lay within the scope of the innovation(s) described in the subject specification. (1) Access through a networked interface (online or otherwise) reduces provisioning lead time and provides a means for customers to update and personalize femto AP autonomously (e.g., free of interaction with technical support entities) at substantially any time. (2) Security against devices attempting to hack into the fetmo AP when networked with it, and support of extensible sharing/networking of the authorization scheme; e.g., white list(s) can be shared. (3) Networked interface (online or otherwise) provides a superior, rich customer experience substantially free of requirement(s) to understand/interpret femto AP programming interface or configuration nomenclature. (4) End user(s) can manage (e.g., remove select covered numbers, or add additional numbers for coverage up to an allotted amount (e.g., upper bound N) for white list(s) associated with the user. (5) Capacity to determine quality of service (QoS), grade of service, or service experience, for specific authorized subscribers. As an example, an identifier for a mobile device that is included in a white list (e.g., white list(s) 220), can have associated utilization logic in a white list profile (e.g., white list profile(s) 222) that ensures the mobile device access femto coverage with guaranteed QoS (e.g., guaranteed packet rate, or guaranteed block error rate) rather than best effort delivery. In an aspect, such capacity can be enabled or provided via white list profile(s) 222. (6) Capacity to check for valid wireless device numbers, codes or tokens (e.g., MSISDNs); subscriber's active numbers, codes or tokens; and numbers, codes or tokens on service accounts in good standing. Such capacity can be provided through networked access to a subscriber database 260, or substantially any other database or data storage accessible to a mobile network that enables coverage through femto access point 130 or a macro cell base station.

White list(s) 220 facilitates management of access to coverage by a femto AP (e.g., femto AP 130) through inclusion of identifiers, e.g., numbers, codes, or tokens, that uniquely identify a mobile device. Various illustrative aspects of the subject innovation based at least in part on a white list concept are discussed next. It is to be noted, notwithstanding, that variations and extensions of such illustrative aspects are possible and are within the scope of the subject innovation.

It is noted that in example system 200, interface component 210, access management component 235, communication platform 255 and network 230, include, or are functionally connected to, a processor (not shown) configured to confer at least in part the described functionality of the various components, and components therein, included in the aforementioned systems. The processor can be configured to execute code instructions stored in a memory (not shown), or a memory component thereon, to provide at least a portion of the described functionality. It should be appreciated that the processor can be a centralized element or be distributed among the above referenced components, server, and platform.

Figure 3:
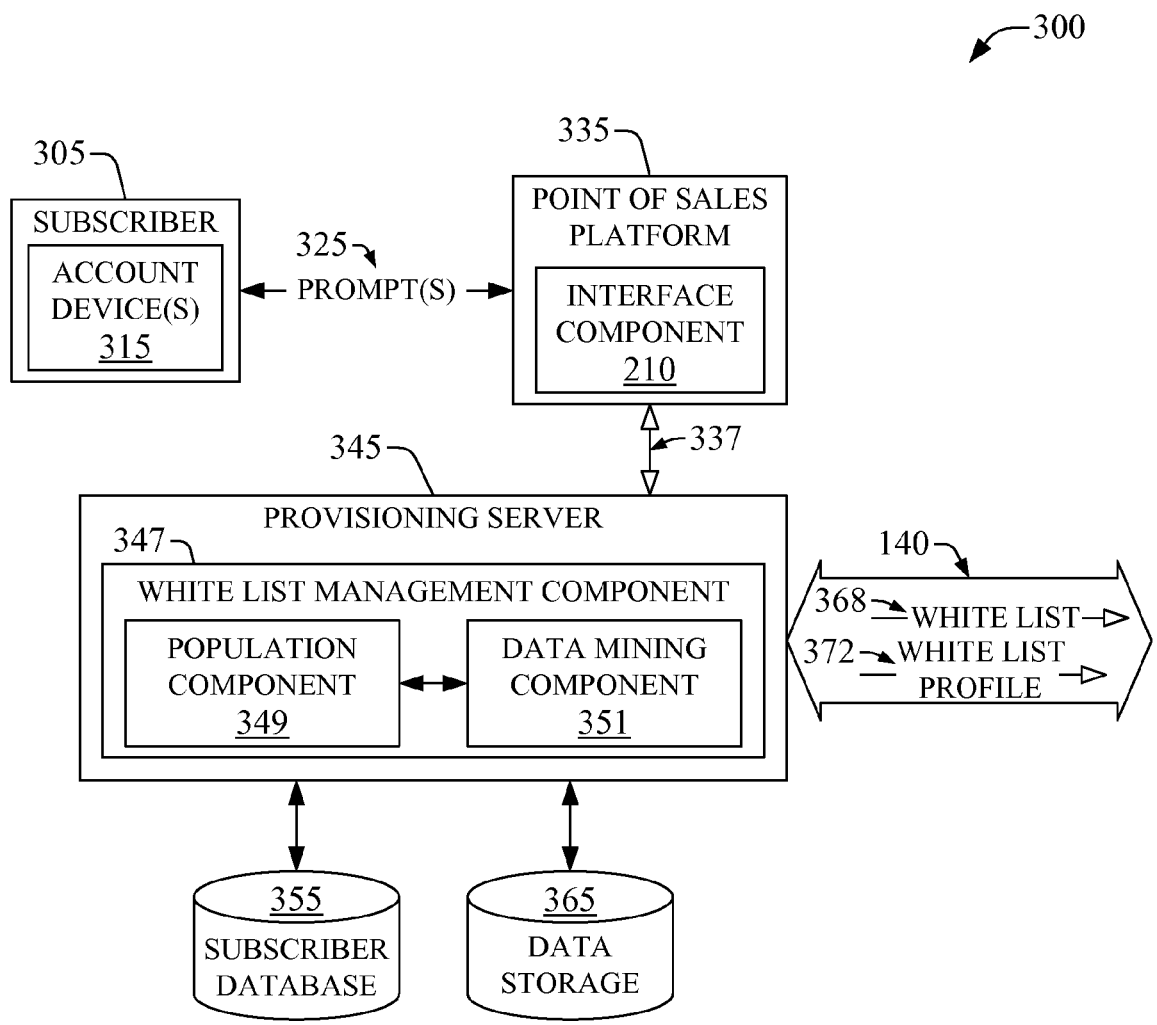
FIG. 3 is a block diagram of an example system that facilitates automatic population of a white list and generation of white list profile in accordance with aspects described herein.

FIG. 3 is a block diagram of an example system 300 that facilitates automatic population of a white list and generation of white list profile in accordance with aspects described herein. In example system 300, subscriber 305 acquires a femto access point from a point of sales 335, and as part of the acquisition subscriber 305 can determine a set of one or more account devices 315 for femto service. Account device(s) 315 are part of the subscriber's service account, which is an account for femto service, and/or macro service, wherein one or more account consumers are billed in accordance to the same billing scheme (e.g., voice and data rating, price point(s) for add-on applications, price point(s) for store on-the-cloud . . . ). As an example, the set of account devices 315 can include handsets and phone numbers (e.g., an international mobile subscriber identity (IMSI) number) that identify the handsets, or cards for wireless service (e.g., subscriber identity module (SIM) cards). It is noted that subscriber 305 can generally access the 10-digit mobile subscriber identification number provided by a network operator, rather than full-length identifier numbers for account device(s) 315. Point of sales 335 includes interface component 210, and is functionally coupled (e.g., networked) through wired or wireless link(s) 337 to a provisioning server 345, which can be one or several network management components within a mobile network platform that provides femto access service. Interface component 210 can prompt, or query, subscriber 305 in connection with establishment of a white list, and receive responses associated thereto. Prompt(s) 325 can be generated by provisioning server 345 through a white list management component 347. In an aspect, prompts are directed to collection of subscriber preferences in connection with configuration of a white list for the set of account devices 315 and identifiers thereof that can be provided by subscriber 305. For instance, subscriber 305 can be prompted whether more than one identifier is available for association with a white list, or access control list, for acquired femto service, and whether a white list is to be automatically populated in case various identifiers are available or a default white list that includes a designated single device is to be generated. In addition, subscriber can be prompted to provide coverage parameters (e.g., logic parameters) to establish logic for utilization of femto coverage by mobile stations associated with provided identifiers. Such parameters can be employed to populate a white list profile that establishes access privileges to femto coverage: For a mobile station linked to a respective identifier number (e.g., MSISDN, IMSI) provided for inclusion in a white list, a coverage parameter can determine one of (1) categories of service (e.g., voice only, data only, voice and data) allowed for a mobile station linked to a respective identifier number (e.g., MSISDN, IMSI); (2) time span of allowed service for a mobile station; (3) telecommunication technologies allowed for use in a femto cell when the mobile station support operation in multiple technologies; and so on.

White list management component 347 can include a population component 349 and a data mining component 351. Population component 349 can accept or reject, e.g., validate, a mobile device identifier intended for a white list, the device identifier provided by subscriber 305 or otherwise, based at least in part on criteria applied to the mobile device. Data mining component 351 can gather information related to the criteria. In an aspect, the criteria can include (i) status of election (e.g., opt in) or non-election (e.g., opt out) flags for inclusion in a white list, wherein status is conveyed, for example, via a K-bit word (K is a natural number) within an entry for the mobile device in a subscriber database; (ii) operational capabilities of the mobile device (e.g., wireless technology utilized by the device such as second generation (2G), third generation (3G), or fourth generation (4G) technologies, radio frequency bands in which the mobile device can receive communications . . . ); (iii) commercial standing (e.g., outstanding bill payments, hotlined mobile device, stolen device); or the like.

In addition, population component 349 can commit an identifier to a white list (e.g., white list(s) 220) as a part of population, or generation, of the white list; in an aspect, the identifier can be committed in a network native format (e.g., full-length digit for a MSISDN or IMSI), or via unique identifier code numbers for the device (e.g., electronic serial number (ESN), international mobile equipment identity (IMEI), or mobile equipment identification (MEID)). It is noted that subscriber 305 is not exposed to such formats. Furthermore, population component 349 can prompt for an indication whether to populate a white list with a single received identifier, all received identifiers or with a subset thereof; prompt(s) can be conveyed through interface component 210. In an aspect, when a prompt request is unanswered (e.g., a timer for response expires, the timer can be implemented by one of white list management component 347 or interface component 210), population component 349 can generate a white list with single identifier on it; the default single identifier can be a phone number of the subscriber that acquires femto access service. Further yet, in an aspect of the subject innovation, population component 349 can prompt for a selection indication to determine a subset of received identifiers when the number of provided identifiers exceeds a predetermined number N of fields configured for white list(s). As a result of the prompt, a selection indication can be received and population component 349 can select the subset of received identifiers. Alternatively, or in addition, population component 349 can automatically select the subset of received identifiers. Selection can be based at least in part on a cut-off procedure in which M (M is a natural number) out of N+M received identifiers are blindly removed from consideration to be included. Cut-off procedure can be complement with confirmation prompt(s) to facilitate selection of identifiers. Still further, population component 349 can correct format of received identifiers to make the contents of the identifiers compliant with a format suitable for a white list or a white list profile.

Population component 349 can format a populated white list 368 or white list profile 372 in accordance with various schemas, such as hypertext markup language (HTML) and extensible markup language (XML) and variants (e.g., state chart XML (SCXML)), that are portable among computing platforms, wireless (e.g., a portable computer or mobile device) or otherwise, and object-oriented computing languages employed by a wireless device such as Delphi, Visual Basic, Python, Perl, Java, C++, and C#, and circuitry programming level languages such as Verilog. Such portability can facilitate straightforward exchange of white lists among subscribers. Extensibility afforded by such formats can facilitate aggregation of white lists, and extraction of at least portions thereof, in web-based applications like blogs, peer-to-peer exchange web applications, and social networking website; it should be appreciated that aggregation and extraction of white lists can be conducted, through data mining component 351 in white list management component 347, as a part of white list administration at the network level.

Provisioning server 345 can receive, through interface component 210, a set of parameters to populate a white list profile associated with a white list generated though population component 349. In an aspect, population component 349 can prompt subscriber 305 to provide parameters that determine characteristics of service (e.g., temporary access, permanent access, specific services . . . ) to be provided to account device(s) 315 entered in a white list (e.g., white list 368). Population component 349 can accept and commit received coverage parameters in order to populate a white list profile 372. When population component 349 terminates population of a white list 368, and generation of an associated white list profile 372, based at least in part on received coverage parameters, provisioning server 345 delivers them to the provisioned femto access point linked to subscriber 305.

In an aspect of the subject innovation, population component 349 can exploit at least in part data mining component 351 to autonomously populate a white list 368 and white list profile 372 associated with subscriber 305 in addition, or in lieu of, received identifiers, and utilization logic parameters, associated with account device(s) 315. To at least that end, in an aspect, data mining component 351 can identify or infer pattern(s) of call (e.g., voice call) activity, and extract a set of frequently called numbers based on the inferred pattern. The pattern contains temporal and spatial information related to each of the frequently called numbers. In addition, pattern includes in-network and out-of-network phone numbers. For out-of-network mobile device numbers, white list management component 347 can convey a request to elect to be added in white list(s); the request can be embodied in a SMS communication, a MMS communication, an email communication, and instant message communication, or the like. Based on status (e.g., opt in, opt out) of election to be included in a white list for each number in the set of frequently called numbers, population component 349 can populate white list 368 with identifiers for those inferred frequently called numbers that allow inclusion in a white list; it should be appreciated that white list 368 populated based upon historic data is an inferred white list that can be edited a posteriori by subscriber 305. It should be appreciated that data mining component 351 can infer a set of identifiers linked to mobile devices based on other data extracted from a set of databases accessible to a service provider. Such set of inferred identifiers can be validated by population component 349 and employed to generate an inferred white list as described above. In addition, in an aspect, data mining component 351 can collect information, e.g., information extant on data storage 365, on technical specifications of each mobile device grouped in the inferred set of frequently called numbers and can establish utilization or coverage parameters to be entered in a white list profile associated with the inferred white list.

In accordance with an aspect of the subject innovation, data mining component 351 can utilize artificial intelligence (AI) methods to infer (e.g., reason and draw a conclusion based at least in part on a set of metrics, arguments, or known outcomes in controlled scenarios) patterns of call activity, relevancy of a mobile device to be added to a white list and/or features suitable to autonomously configure a white list profile for the mobile device based at least in part upon mobile device operation capabilities and past mobile service(s) usage. Artificial intelligence techniques typically can apply advanced mathematical algorithms—e.g., decision trees, neural networks, regression analysis, principal component analysis (PCA) for feature and pattern extraction, cluster analysis, genetic algorithm, and reinforced learning—to historic and/or current data associated with mobile devices served by a mobile network platform at the macro or femto level to facilitate rendering an inference(s) related to the mobile devices.

In particular, data mining component 351 can employ one of numerous methodologies for learning from data and then drawing inferences from the models so constructed, e.g., Hidden Markov Models (HMMs) and related prototypical dependency models. General probabilistic graphical models, such as Dempster-Shafer networks and Bayesian networks like those created by structure search using a Bayesian model score or approximation can also be utilized. In addition, linear classifiers, such as support vector machines (SVMs), non-linear classifiers like methods referred to as "neural network" methodologies, fuzzy logic methodologies can also be employed. Moreover, game theoretic models (e.g., game trees, game matrices, pure and mixed strategies, utility algorithms, Nash equilibria, evolutionary game theory, etc.) and other approaches that perform data fusion, etc., can be exploited in accordance with implementing various automated aspects described herein.

In addition, data mining component 351, via population component 349, can prompt subscriber 305 through prompt(s) 325 to make data or information local to each of account device(s) 315 in order for white list management component 347 collect data to facilitate population of a white list. In an aspect, data can include address book(s), call activity log(s), or the like. When subscriber 305 delivers via interface component 210 an indication (e.g., a multi-bit word) of approval to collect data, data mining component 347 gathers the data and analyzes the data to extract a set of likely identifiers (e.g., MSISDNs, IMSIs, ESNs, IMEIDs . . . ) to automatically populate the white list. Analysis can include computation of statistics associated with call activity, identification of call patterns, or verification of opt-in status for mobile devices associated with extracted identifiers. Once identifiers are available, a white list can be populated and an associated white list profile can be constructed (e.g., inferred and populated).

It is noted that in example system 300, provisioning server 345 or components therein, interface component 210, include, or are functionally connected to, a processor (not shown) configured to confer at least in part the described functionality of the various components, and components therein, included aforementioned systems. The processor can be configured to execute code instructions stored in a memory (not shown), or a memory component thereon, to provide at least a portion of the described functionality. It should be appreciated that the processor can be a centralized element or be distributed among the various components, server, and platform.

Figure 4A:
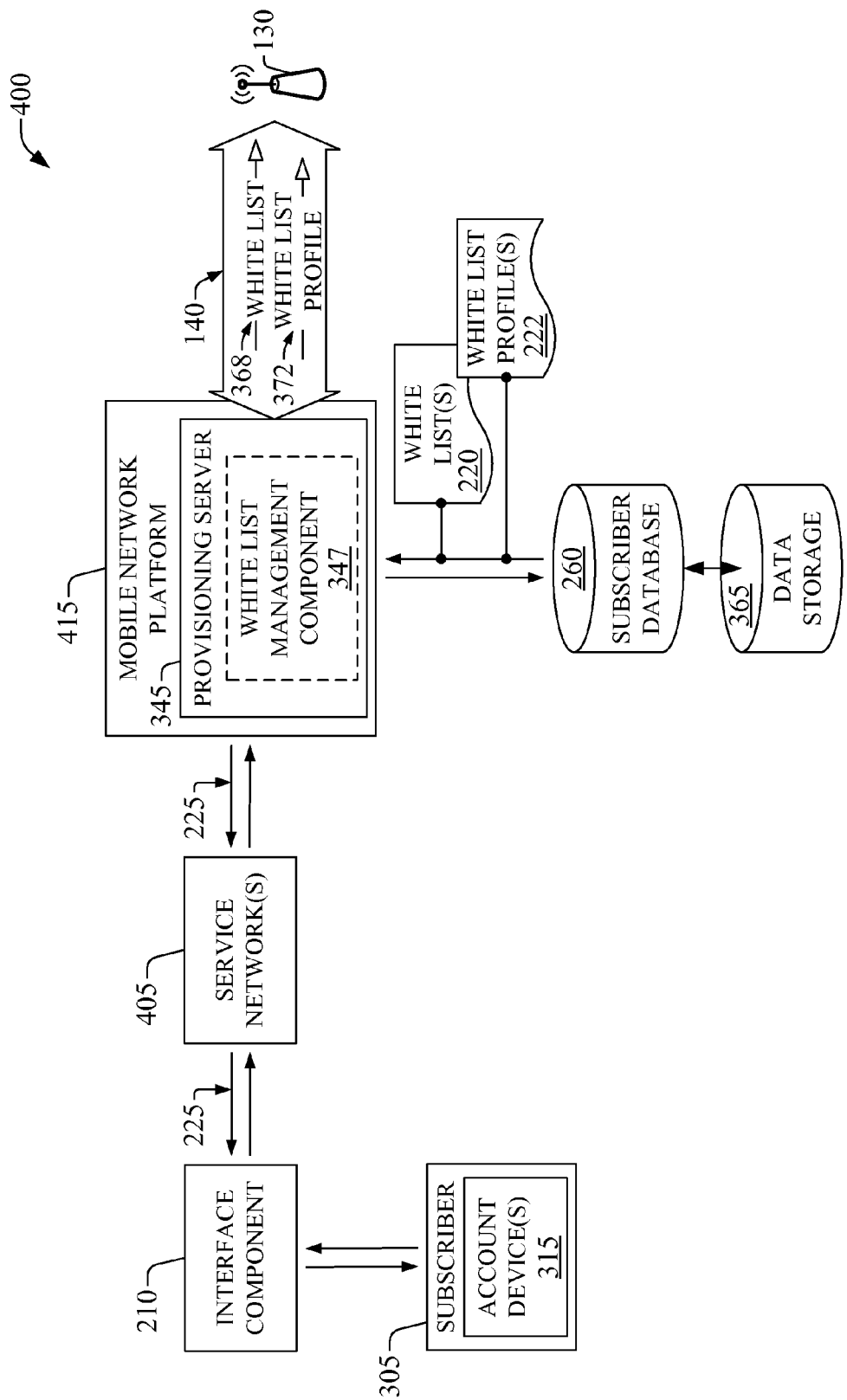
FIGS. 4A-4B are block diagram of an example systems that automatically populates, or initializes, white list(s) and associated white list profile(s) to manage femto coverage service in accordance with aspects described herein.

FIG. 4A is a block diagram of an example system 400 that populates, or initializes, access control list(s), or white list(s), to femto coverage service provided with available subscriber station identifier numbers, codes or tokens received through an interface component 210. In example system 400, a subscriber can access interface component 210 which can be administered by service network(s) 405. In an aspect, interface component 210 can be a web-based interface and access can be accomplished via secure login (e.g., virtual private network, secure file transfer, secure copy . . . ) supported by service network(s) 405. In an aspect, service network(s) 405 can be substantially any, or any network (e.g., non-mobile broadband internet service provider, local area network, etc.) that can be linked to mobile network platform 415. Network link 225, which can be embodied in a Gi reference link, attaches service network(s) 405 to mobile network platform 415. A set of identifiers associated with account device(s) 315 or otherwise, is then conveyed to white list management component 347. As described above in connection with operation of white list management component 347, white list(s) 220, and associated white list profile(s) 222 can be generated in substantially the same manner as described above in connection with example system 300.

It is noted that in example system, identifiers (e.g., MSISDNs, IMSIs, ESNs, IMEIs), codes or tokens can be gleaned from subscriber database 260 through the secure connection established among subscriber 305, via interface component 210, and white list management component. Subscribers that present election flags that decline inclusion in white list(s) are not provided for subscriber 205 to browse. Additionally, to further ensure privacy, partial identifiers in conjunction with a selector component (not shown) can be provided to subscriber 305 to provide identifiers associated with mobile device that opted in to white list management component 347. Once valid identifiers are provided to white list management component 347, white list(s) 220 and associated white list profile(s) 222 can be automatically populated as described above in connection with example system 300.

As discussed above, white list management component 347 can prompt subscriber 305 through network link(s) 225 to make available data or information local to each of account device(s) 315 in order to facilitate population of white list(s) 220 and construct (e.g., infer and populate) white list profile(s) 222. In an aspect, data can include address book(s), call activity log(s), or the like.

Figure 4B:
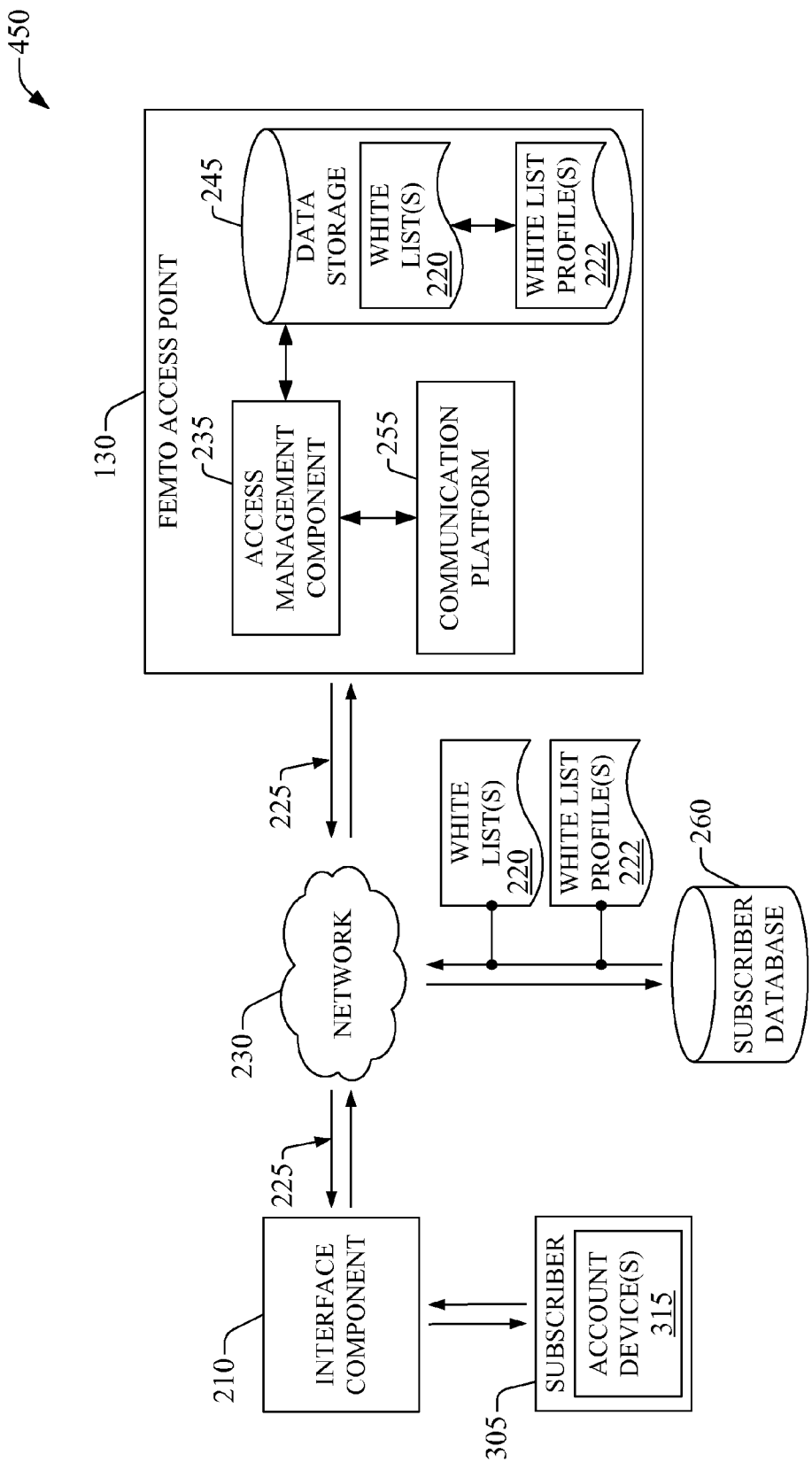

FIG. 4B is a block diagram of an example system 450 that initializes access control list(s), or white list(s), to femto coverage with available subscriber station identifier numbers, codes or tokens available on a service account (e.g., account of subscriber 305). In example system 450, a subscriber 305 who utilizes account device(s) 315, can provision femto AP 130 and associate account device(s) 315 with a service account via a networked interface component 210 (e.g., an online account management system) which can look up into substantially all subscriber station(s) identifier numbers (e.g., MSISDNs), codes or tokens associated with the service account, and automatically populates white list(s) 220 with the extracted subscriber station(s) numbers, codes or tokens. Subscriber 305, via interface component 210, can remove or add subscriber station(s) numbers (e.g., MSISDNs), codes or tokens extant in a pre-populated white list(s) 220; additional edits can be performed as well, based at least in part on the complexity of white list(s) 220 and desired access privileges to femto coverage, provided by femto AP 130, that are to be conferred to whitelisted (e.g., included in white list(s) 220) mobile devices as dictated by white list profile(s) 220. In an aspect, to pre-set white list(s) 220, networked interface component 210 access information stored in subscriber database 260 through network 230 which can include information technology systems of a service provider, and data storage related to service network(s) (e.g., internet protocol (IP) multimedia subsystem (IMS)) that provide services to a mobile network platform administered by the service provider. As discussed above, white list(s) 220 and white list profile(s) 222 are conveyed through network 230 via network link(s) 225 to femto access point 130; a communication platform receives white list(s) 220, and access management component 235 stores the white list(s) 220 and white list profile(s) 222 in data storage 245.

Illustrative advantages provided by the foregoing example systems 400 and 450 are (a) reduced femto cell provisioning lead time, and (b) immediate utilization of a femto cell with mobile numbers that belong to a same service account, with the ensuing billing simplifications (e.g., bundle pricing, voice credits reutilization or transfer among whitelisted (e.g., committed to a white list(s)) numbers, etc.); operation monitoring capabilities (e.g., a parent can monitor usage of voice and data services through femto AP 130 of a child) which can be set through parameter(s) in a white list profile such as white list profile(s) 222; enhanced indoor wireless coverage; and so forth; whether subscribers of such numbers subscribe to the femto cell or a feature application, or code, that delivers a femto cell service.

It is noted that in example systems 400 and 450, provisioning server 345, service network(s) 405, networks(s) 230, and mobile network platform 415 include, or are functionally connected to, a processor (not shown) configured to confer at least in part the described functionality of the various components, and component therein, included aforementioned systems. The processor can be configured to execute code instructions stored in a memory (not shown), or a memory component thereon, to provide at least a portion of the described functionality. It should be appreciated that the processor can be a centralized element or be distributed among the various referenced systems, component, networks, and platform.

In view of the example systems described above, example methodologies that can be implemented in accordance with the disclosed subject matter can be better appreciated with reference to flowcharts in FIG. 5-10. For purposes of simplicity of explanation, the example methodologies, or methods, are presented and described as a series of acts; however, it is to be understood and appreciated that the claimed subject matter is not limited by the order of acts, as some acts may occur in different orders and/or concurrently with other acts from that shown and described herein. For example, it should be understood and appreciated that a methodology, or method, could alternatively be represented as a series of interrelated states or events, such as in a state diagram, or interaction diagram. Moreover, not all illustrated acts may be required to implement a methodology in accordance with the subject specification. Additionally, it is noted that two or more methodologies, or methods, can be enacted in conjunction. Furthermore, it should be further appreciated that the methodologies, or methods, disclosed hereinafter and throughout this specification are capable of being stored on an article of manufacture to facilitate transporting and transferring such methodologies, or methods, to computers for execution by a processor or for storage in a memory.

Figure 5:
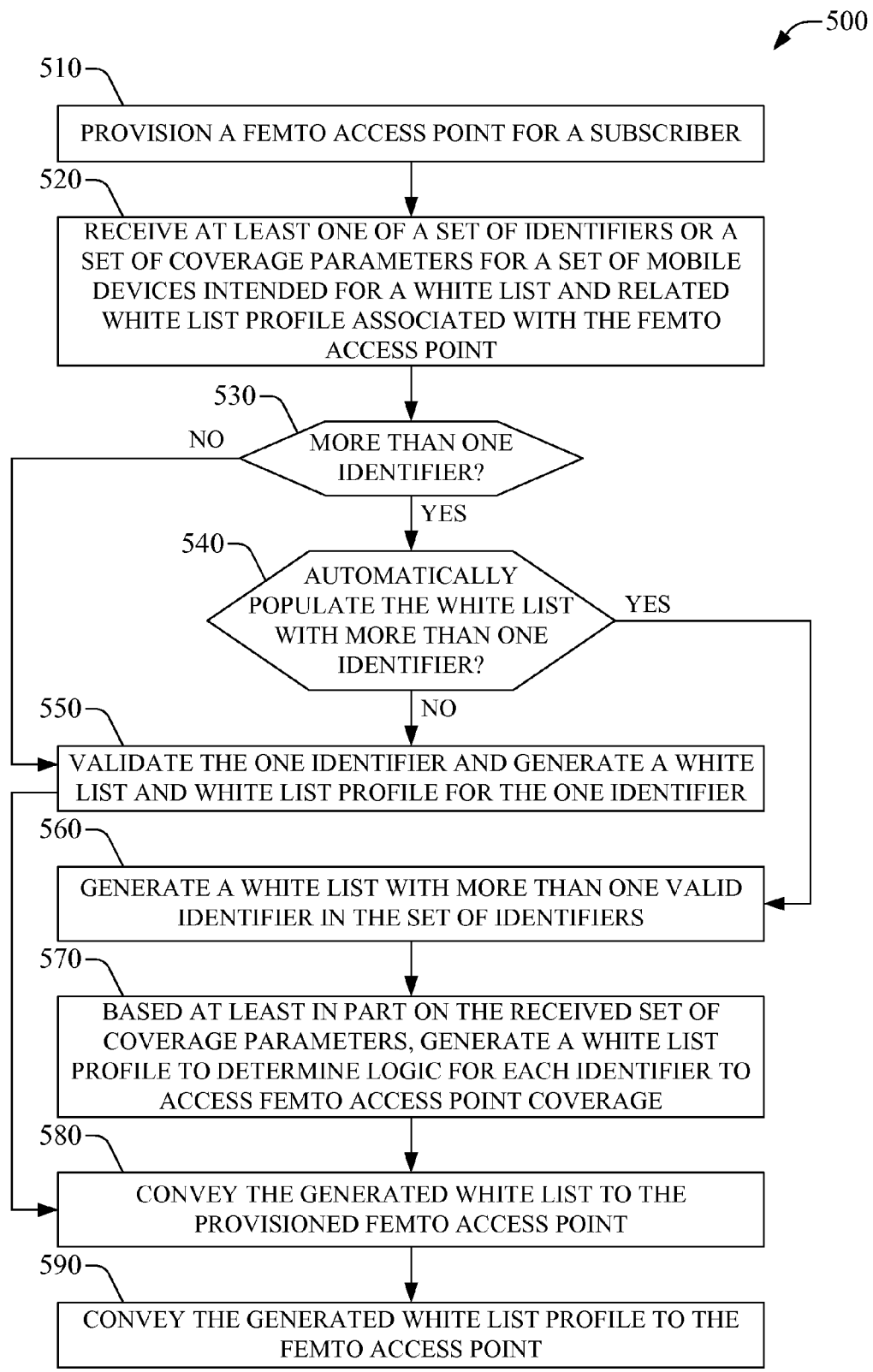
FIG. 5 is a flowchart of an example method for automatically populating a white list and a white list profile according to aspects described herein.

FIG. 5 is a flowchart of an example method 500 for automatically populating a white list and a white list profile according to aspects described herein. The subject example method 500 can be enacted by a component within a mobile network platform (e.g., a core network in cellular technologies such as 3GPP UMTS, 3GPP Long Term Evolution (LTE), 3rd Generation Partnership Project 2 (3GPP2) Ultra-Mobile Broadband (UMB)). At act 510, a femto access point is provisioned for a subscriber. The subscriber can acquire the femto AP (e.g., femto AP 130) at the time of provisioning, or at a prior time. At act 520, at least one of a set of identifiers or a set of coverage parameters are received for a set of mobile devices intended for a white list and related white list profile associated with femto coverage through the femto access point; the set of coverage parameters are associated with the set of identifiers. The set of identifiers can include mobile subscriber identification numbers like MSISDNs or IMSIs, or codes or tokens that uniquely identify a mobile device at the hardware level, such as ESN, IMEI, MEID, or the like. Coverage parameters can establish access privileges to femto coverage; privileges can include type of service, time span of coverage, technologies allowed to be employed within coverage area, etc. In an aspect, the subject act can include prompting a subscriber to provide the identifiers and coverage parameters; prompting can be generated by a component that manages white list(s) (e.g., white list management component 347) and effected through an interface component (e.g., interface component 210).

At act 530, it is checked whether more than one identifier is received. In the affirmative case, at act 540, it is checked whether the white list is to be automatically populated with more than one identifier. In an aspect, a component (e.g., population component 349 or white list management component 347) can determine a number of received identifiers, and the component also can facilitate act 540 by prompting a source of identifiers for input regarding a number of identifiers to be employed for automatically populating a white list. When outcome of act 540 is negative, the one identifier is validated and a white list and white list profile are generated for the one identifier at act 550. In an aspect, validation includes at least one of verifying a mobile device associated with the one identifier is flagged to opt in for inclusion in femto access service, or identifying commercial standing (e.g., outstanding bill payments, hotlined mobile device, stolen device) of the mobile device associated with the one identifier allows the one identifier to be entered in a white list. In case outcome of act 540 is positive, a white list with more than one valid identifier in the set of identifiers is generated. When outcome of act 530 is negative, act 550 is enacted as described above and flow is directed to act 580, in which the generated white list is conveyed to the provisioned femto access point.

At act 570, based at least in part on the received set of coverage parameters, a white list profile is generated to determine logic for each identifier to access femto access point coverage. In an aspect, such logic determines at least one of time intervals for each identifier to access femto coverage; privileges to access voice and data services provided through the provisioned access point, wherein the privileges dictate degree of access to a service such as QoS profile (e.g., best effort or guaranteed quality of service); allocated bandwidth; preemption profile or relative priority of access to service (e.g., video streaming, sound streaming, voice . . . ) for various mobile devices in a white list, emergency calls are not preempted; or the like. In another aspect, when the set of received coverage parameters is the empty set or no coverage parameters are received, a default white list profile can be generated, wherein each mobile station associated with an identifier in a white list related to the white list profile is allowed full access to femto service or coverage; the full access dictated by a service plan acquired by a subscriber for which the femto AP is provisioned. A generated white list that includes more than one identifier also is conveyed at act 580, while at act 590, the generated white list profile is conveyed to the provisioned femto access point. It should be appreciated that the generated white list profile conveyed in the subject act can be associated with either a one identifier white list or with a white list that includes more than one identifier.

Figure 6:
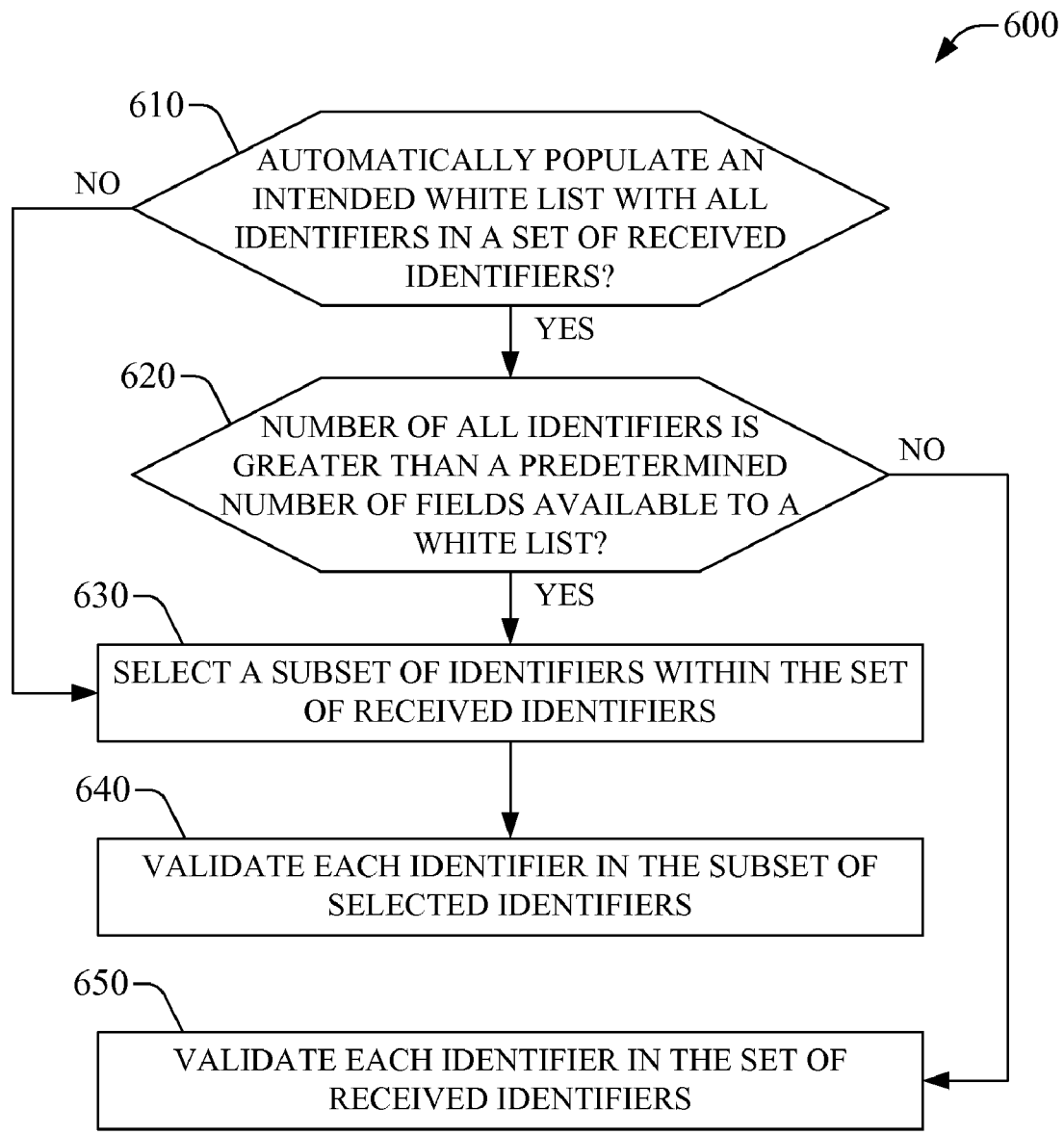
FIG. 6 is a flowchart of an example method to determine valid identifiers in instances when a white list is to be automatically populated with more than one identifier according to aspects described herein.

FIG. 6 is a flowchart of an example method 600 to determine valid identifiers in instances when a white list (e.g., white list 220) is to be automatically populated with more than one identifier according to aspects described herein. It should be appreciated that the subject example method 600 can be utilized in conjunction with at least example method 500, particularly in connection with act 560.

At act 610, is it evaluated whether an intended white list is to be automatically populated with all identifiers in a set of received identifiers. In an aspect, the identifiers are received through an interface component accessed via a point of sales platform (e.g., platform 335) or through a service network (e.g., an internet service provider network) linked to a mobile network platform that automatically populates a white list. An affirmative outcome to evaluation act 610 leads to additional evaluation act 620, wherein it is probed whether number of all identifiers is greater than a predetermined number N of fields (e.g., N=50) available to a white list; the upper bound N can depend at least in part on the revenue segment (e.g., high-end revenue or premium subscriber, low-end revenue . . . ) a subscriber that provides the set of identifiers operates in. It is noted that the upper bound N also can be dynamics, presenting fluctuations around a typical value for a subscriber, wherein the magnitude of the fluctuations can be based upon newly available network resources. A positive outcome to act 620 leads to act 630 in which a subset of identifiers within the set of received identifiers is selected. A negative outcome of act 620 directs flow to act 650, at which each identifier in the set of received identifiers is validated; validation proceeds in substantially the same, or the same, manner as described above. With respect to act 610, a negative outcome directs flow to act 630. At act 640, each identifier in the subset of selected identifiers is validated; validation proceeds in substantially the same, or the same, manner as described above.

Figure 7:
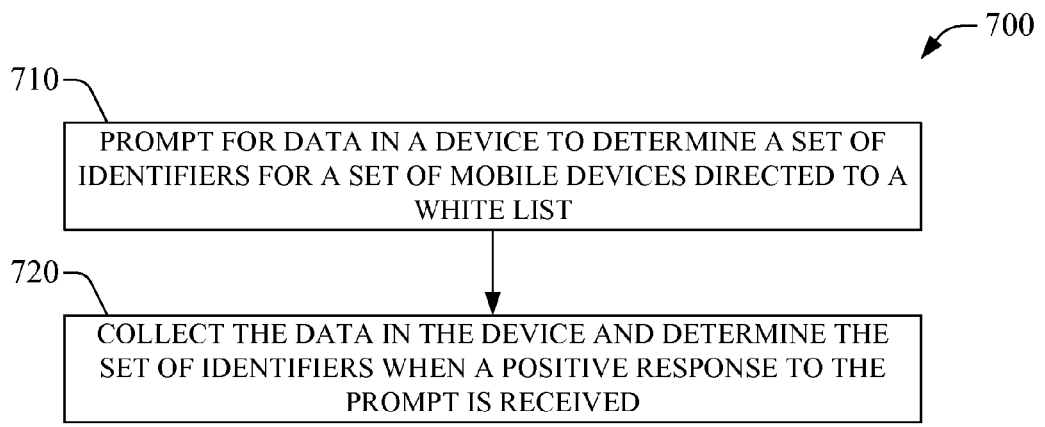
FIG. 7 presents a flowchart of an example method for automatically generating a set of identifiers directed to a white list to be populated without subscriber actively providing the set of identifiers according to aspects described herein.

FIG. 7 presents a flowchart of an example method 700 for automatically generating a set of identifiers directed to a white list to be populated without subscriber actively providing the set of identifiers according to aspects described herein. It should be appreciated that the subject example method can be utilized in conjunction with almost any example method described herein. At act 710, data (e.g., an address book, a call log . . . ) in a device, which can be mobile or otherwise, is prompted for to determine a set of identifiers for a set of mobile devices directed to a white list; the white list can be associated with a provisioned femto access point. In an aspect, a subscriber that provisioned the femto access point is prompted for the data. In an aspect, a prompt (e.g., prompt(s) 325) can be delivered by an interface component functionally connected to the device, mobile or otherwise, operated by the subscriber. At act 720, when a positive response to the prompt is received, the data in the device, mobile or otherwise, is collected and the set of identifiers is determined.

Figure 8:
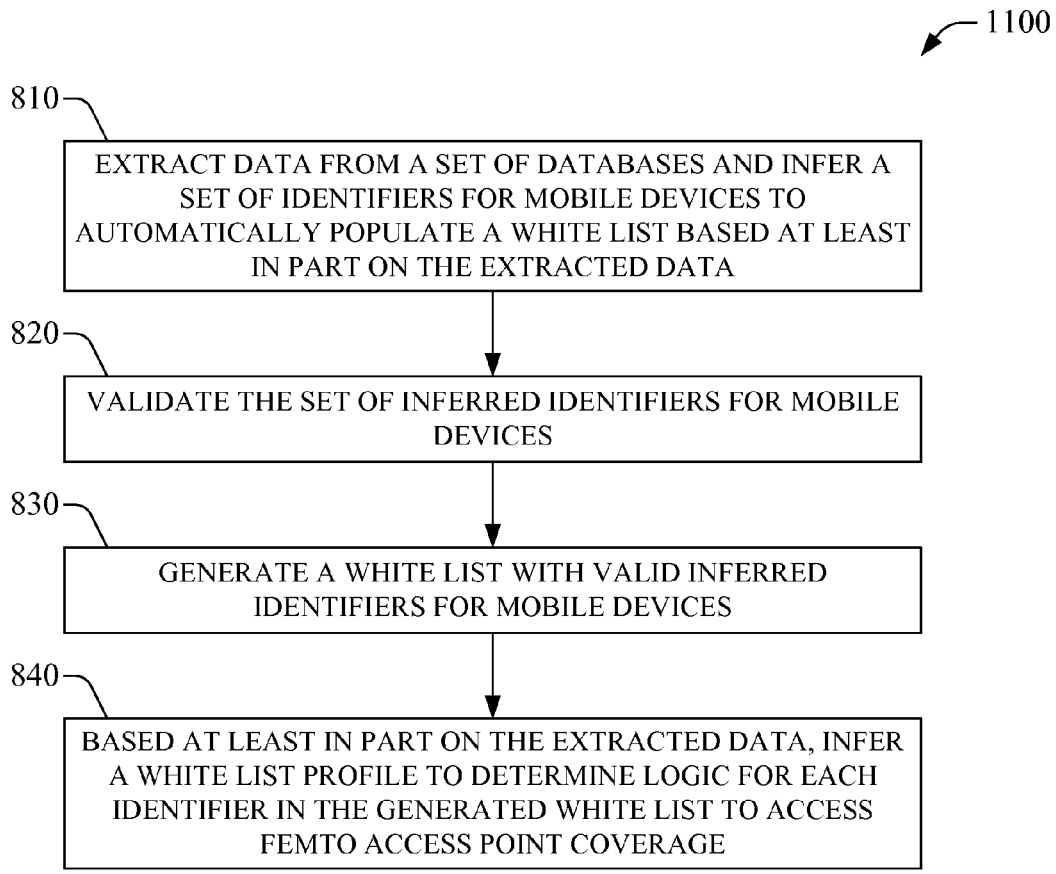
FIG. 8 is a flowchart of an example method for autonomously populating a white list and generating an associated white list profile according to aspects described herein.

FIG. 8 is a flowchart of an example method 800 for autonomously populating a white list and generating an associated white list profile according to aspects described herein. It should be appreciated that the subject example method can be utilized in conjunction with almost any example method described herein. At act 810, data is extracted from a set of databases and a set of identifiers for mobile devices to automatically populate a white list is inferred based at least in part on the extracted data. In an aspect, the databases associated with a subscriber for which a femto access point is provisioned. Extracted data can include historic data on calling activity for the subscriber that provisions a femto access point, and patterns thereof. In addition, or alternatively, the databases are related to subscribers of macro coverage; the subscribers can be related to the subscriber that provisions a femto access point. In another aspect, inference can be performed by a white list management component or a component therein (e.g., data mining component 351). Inference can rely at least in part on machine learning algorithms. At act 820, the set of inferred identifiers for mobile device is validated. In an aspect, validation proceeds as discussed above. At act 830, a white list with valid inferred identifiers for mobile devices is generated. In an aspect, white list generation can be enacted by a white list management component or a component therein (e.g., data mining component 351). At act 840, based at least in part on the extracted data, a white list profile to determine logic for each identifier in the generated white list to access femto access point coverage is inferred. As discussed above, the logic can establish coverage privileges when the mobile devices associated with the identifiers committed to the generated white list are served by the provisioned femto AP that can retain the generated white list.

Figure 9:
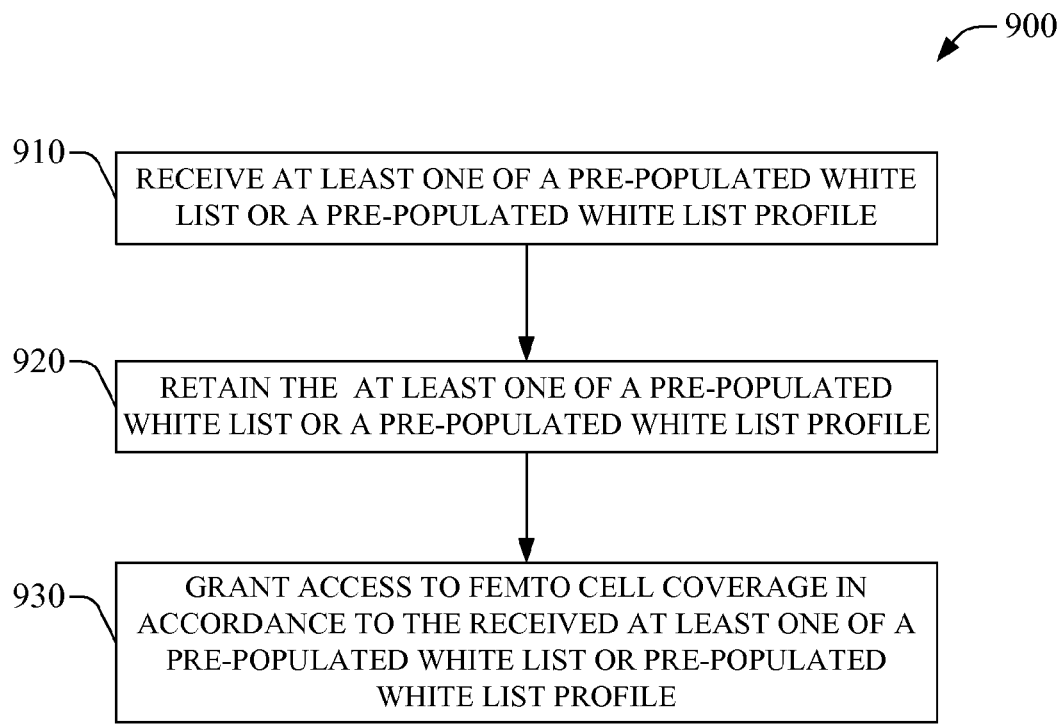
FIG. 9 is a flowchart of an example method for utilizing a white list or associated white list profile to manage access to femto access point coverage of subscriber stations and related subscribers according to aspects described herein.

FIG. 9 presents a flowchart of an example method 900 for utilizing a white list to manage access to femto access point coverage of subscriber stations and subscribers according to aspects described herein. In an aspect, the subject example method can be enacted by the femto access point (e.g., femto AP 130) that exploits the pre-populated white lists. It is noted that the subject example method 900 can be utilized with white list(s) and white list profile(s) that are pre-populated but rather configured in various manners as described in the subject specification. At act 910, at least one of a pre-populated white list or a pre-populated white list profile are received. In an aspect, a communication platform (e.g., communication platform) within the femto access point receives and processes signals that carry the contents of the pre-populated white list and pre-populated white list profile. At act 920, the at least one of a pre-populated white list or a pre-populated white list profile are retained. A memory, in the femto access AP can retain the white list and associated white list profile. At act 930, access to femto cell coverage is granted in accordance with the received at least one of a pre-populated white list or pre-populated white list profile.

Figure 10:
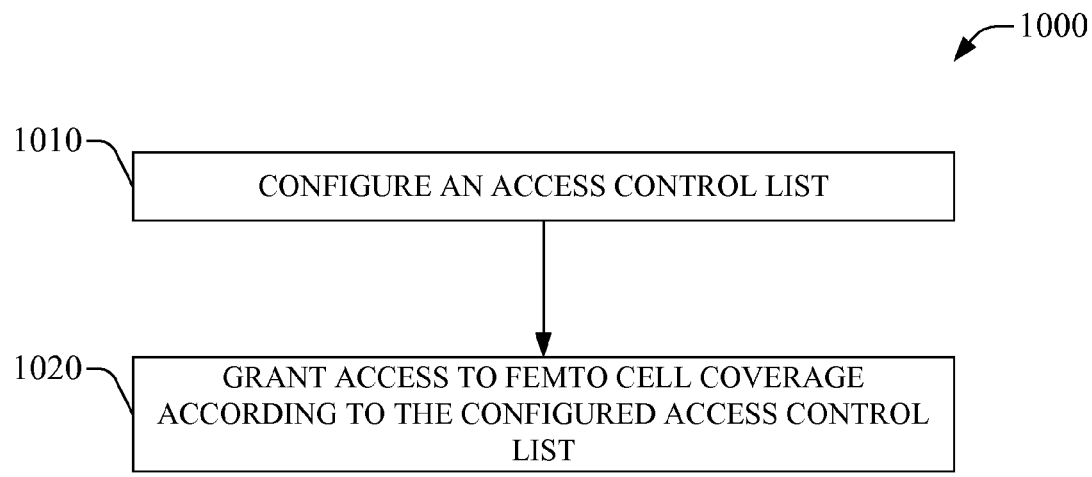
FIG. 10 presents a flowchart of an example method for managing access of subscribers and subscriber stations to femto cell coverage according to aspects described herein.

FIG. 10 presents a flowchart of an example method 1000 for managing access of subscribers and subscriber stations to femto cell coverage. At act 1010 an access control list, or white list, for a femto cell is configured. In an aspect, the subject example method can be enacted by the femto access point (e.g., femto AP 130) that exploits the pre-populated white lists. In another aspect, configuration can be performed via a networked interface, interactively or automatically based at least in part on operation conditions of the femto cell; e.g., initial provisioning, capturing of wireless devices, responding to request for access, updating extant access control lists, and so forth. At act 1020, access to femto cell coverage is granted according to the configured access control list. In another aspect, the configured access control list can possess an associated profile, e.g., white list profile 222, that controls logic for utilization of the access control list, via a set of parameters that determine conditions of access, type of access, etc., as described herein.

Figure 11:
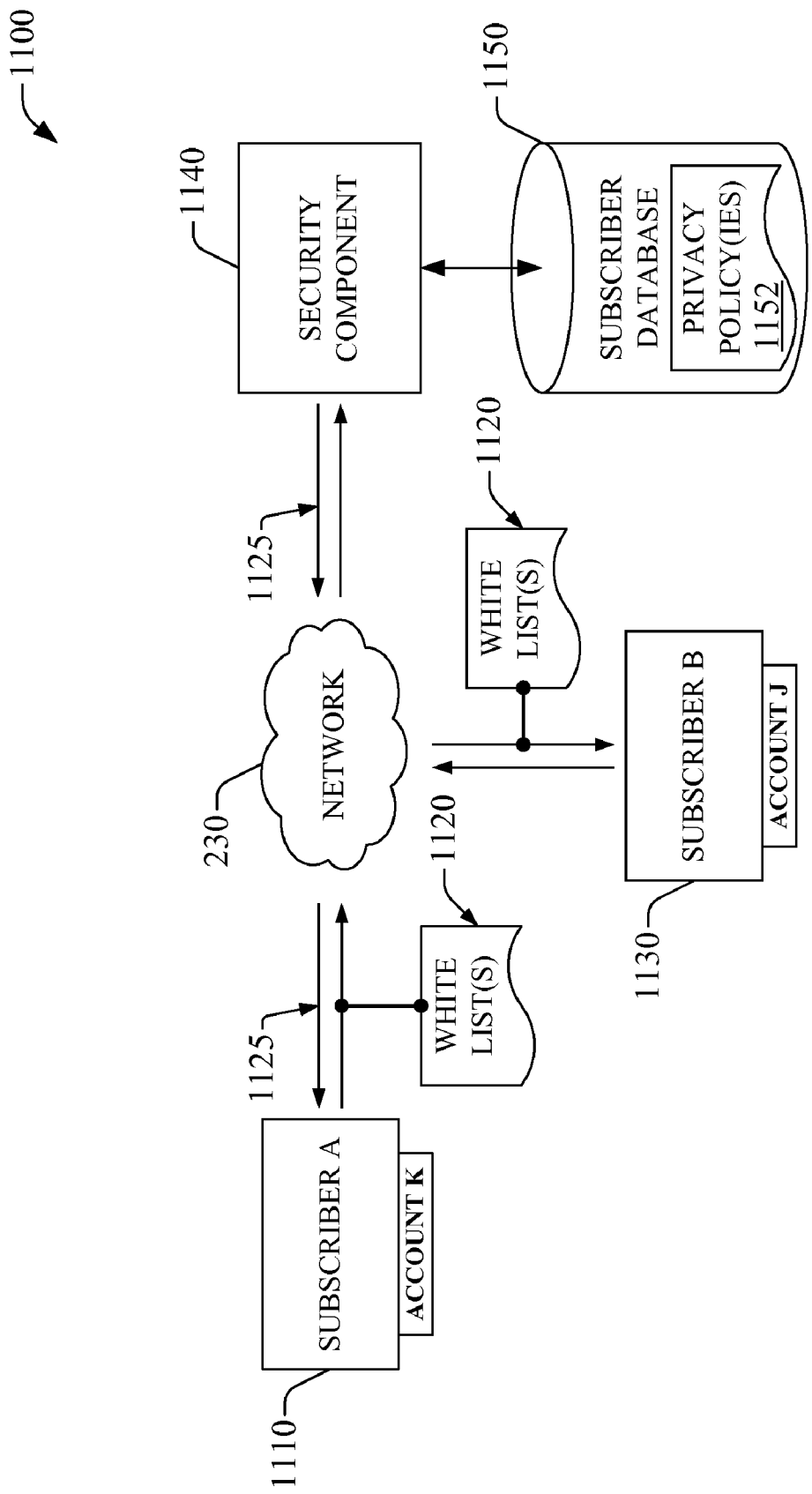
FIG. 11 is a block diagram of an example system to share access control list(s), or white list(s), in accordance with aspects described herein.

FIG. 11 is a block diagram of an example system 1100 to share access control list(s), or white list(s) 1120, among subscribers of a wireless network service in order to provide straightforward access configuration to, and activation of, a femto cell (e.g., femto AP 130) among femto cell subscribers. Subscribers can belong to disparate or same service accounts with either a macro service provider or femto provide, or both. For example, subscribers that share white list(s) 1120 can pertain to a group or family associated with a single service account. In example system 1100, subscriber A 1110 who belongs to account K conveys white list(s) 1120 over network 230, via a wired or wireless link 1125, to subscriber B 1130 who belongs to account J. Subscriber A 1110 can hide or eliminate specific subscriber station numbers from white list(s) 1120 he/she/it grants to other subscribers. It should be appreciated that the granting of subscriber station numbers (e.g., MSISDNs, IMSIs . . . ), codes or tokens can substantially reduce the amount of time to configure, or set up a white list, as opposed to manually re-entering multiple (e.g., up to 50 numbers, codes or tokens) across multiple femto cells.

A security component 1140, or authorization layer, can ensure that unauthorized mobile subscriber numbers (e.g., MSISDNs, IMSIs . . . ), codes or tokens, are not provided when not approved by end users. In an aspect, security component 1140 can generate election flags that reflect whether a mobile station can be added to a white list. Such approval can be determined via a privacy policy(ies) 1152 associated with the end user, or subscriber linked to a mobile device, which can be stored in a subscriber database 1150; the privacy policy can be configured/updated through various means like web-based interfaces, call center, text-message center, and so on. Security component 1140 ensures privacy integrity when white list(s) 1120 are shared among subscribers of different accounts (e.g., $J \neq K$). In an illustrative aspect, security component 1140 can solicit, or prompt, subscribers outside a "white-list share" originating account to grant the authority for their subscriber station identifier number, code or token to be shared through white list(s). To the latter end, security component 1140 can resort to various mechanisms that include, but are not limited to including, a short message service (SMS) communication, a multimedia message service (MMS) communication, instant message (IM) communication, email, voice mail, web pop up, and so on. Alternatively, or in addition, security component 1140 can mitigate security mechanism(s) complexity through validation via subscriber account information such as election (e.g., opt-in/opt-out) flags (e.g., stored in subscriber database 1150) in order to grant automatic access to white list(s) within groups or families underneath a single service account, without additional security verification.

Figure 12:
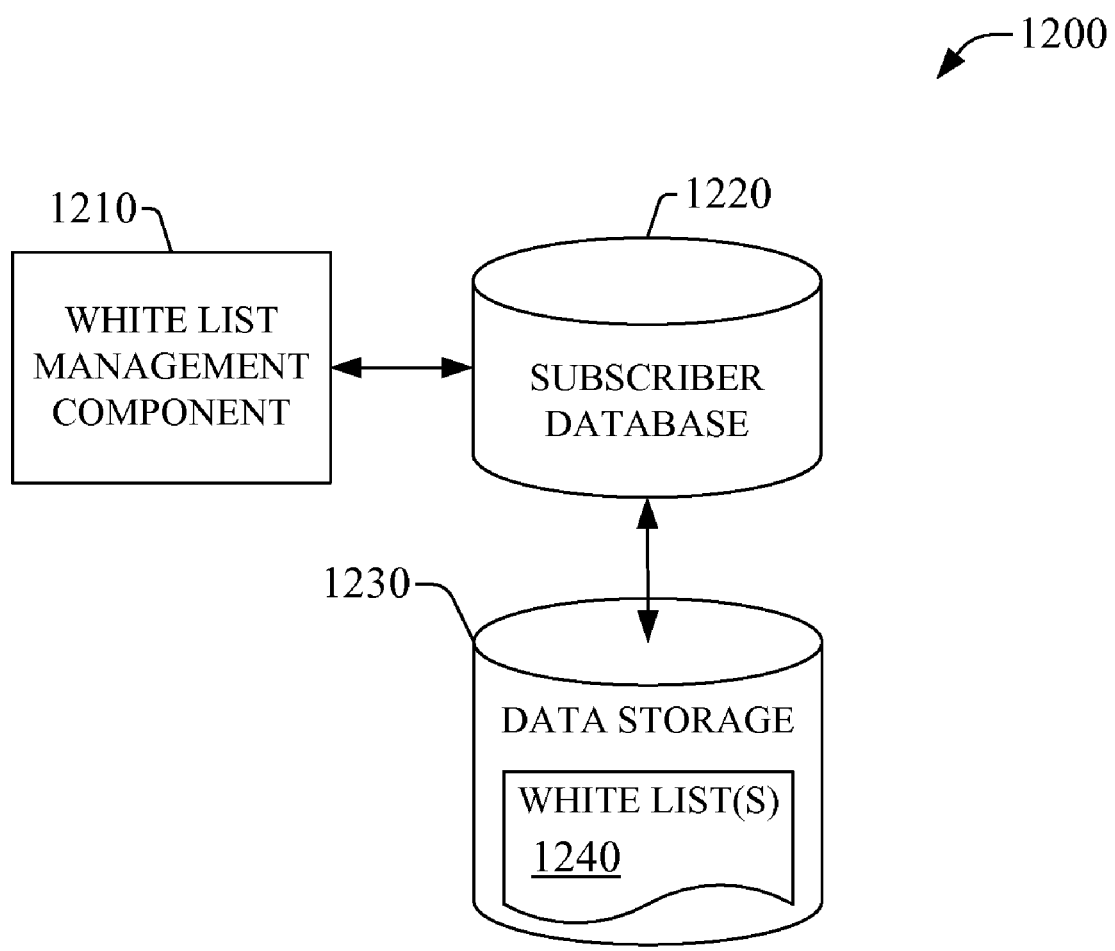
FIG. 12 is a block diagram of an example system that manages access control lists, or white lists, in accordance with aspects described herein.

FIG. 12 is a block diagram of an example system 1200 that manages access control lists, or white lists (e.g., white list(s) 1240) in accordance with aspects described herein. White list management component 1210, via for example data mining component 351, can access a subscriber database 1220 which can be maintained by a service operator for femto and macro networks, and a data storage 1230 that retains a set of white lists 1240 associated with served subscribers, to associate whitelisted subscribers across disparate access control lists, or white lists. It should be appreciated that data storage 1230 can be associated with various network platforms linked to a mobile network platform operated by the service provider. Such association can lead to genesis of white-lists trees. In an aspect, white list management component 1220 can implement mechanisms to mitigate exponential data growth and efficient storage of white-list trees like data-compression (e.g., wavelet, efficient tree representation, and so on), distributed data warehouses, and so forth. In another aspect, white list management component 1220 can deploy a white-list tree in accordance to the following illustrative, non-limiting scenario. (i) User 1 adds User 2 to his/her white list. (ii) User 2 adds User 3 to his/her white list. (iii) User 1 and User 3 can be associated through white lists. (iv) User 1 and User 3 can match User 4 extant on each other's white lists. (v) User 1 and User 3 can associate User 5 that is on User 4's white list. White list management component 410 effects associations and manages generated white-list tree(s). It should be appreciated that substantially any association, hierarchical or non-hierarchical, or deployment of white lists (e.g., white list(s) 1240) can be implemented by white list management component 1210 through information stored in subscriber database 1220 and data storage 1230.

An illustrative, non-limiting, advantage of structured, hierarchical generation of white lists to subscribers (e.g., subscriber A 1110) is that more subscribers can have access femto cells to gain coverage enhancement, or have access to added value through unlimited usage on any femto cell or unique services available via a set of femto cells.

In addition, example system 1200 can track subscriber station identifier numbers (e.g., MSISDNs, IMSIs), codes or tokens, associated with white list(s) on record with a femto service provider. White list management component 1210 can validate white list(s) 1240, stored in data storage 1230, against current accounts and associated subscriber station identifier numbers (e.g., MSISDNs, IMSIs), codes, or tokens, for a service provider. In particular, when a subscriber (e.g., subscriber A 1110), or end user, cancels an account with service provider, white list(s) 1240 can be updated according to information retrieved from subscriber database 1220, which is updated as a result of the cancelled subscription, or substantially any other database available to a service provider that contains information on service subscribers. In addition, when an end user changes their mobile or subscriber station number, code or token, (e.g., after relocation to a new area code, or the like) substantially all white list(s) 1240 that the mobile or subscriber station number, code or token is associated with can automatically be updated by white list management component 1210.

An illustrative advantage of such automatic update of white list(s) 1240 is ease of use for end users to maintain current white list(s) 1240 without a need to keep track of each subscriber station number, code, or token associated with the white list(s) 1240. In addition, updated white list(s) 1240 maintains the value proposition of the femto cells for end users and service operator by a seamless move of traffic off of the macro network (e.g., a WAN) to femto network(s).

Figure 13:
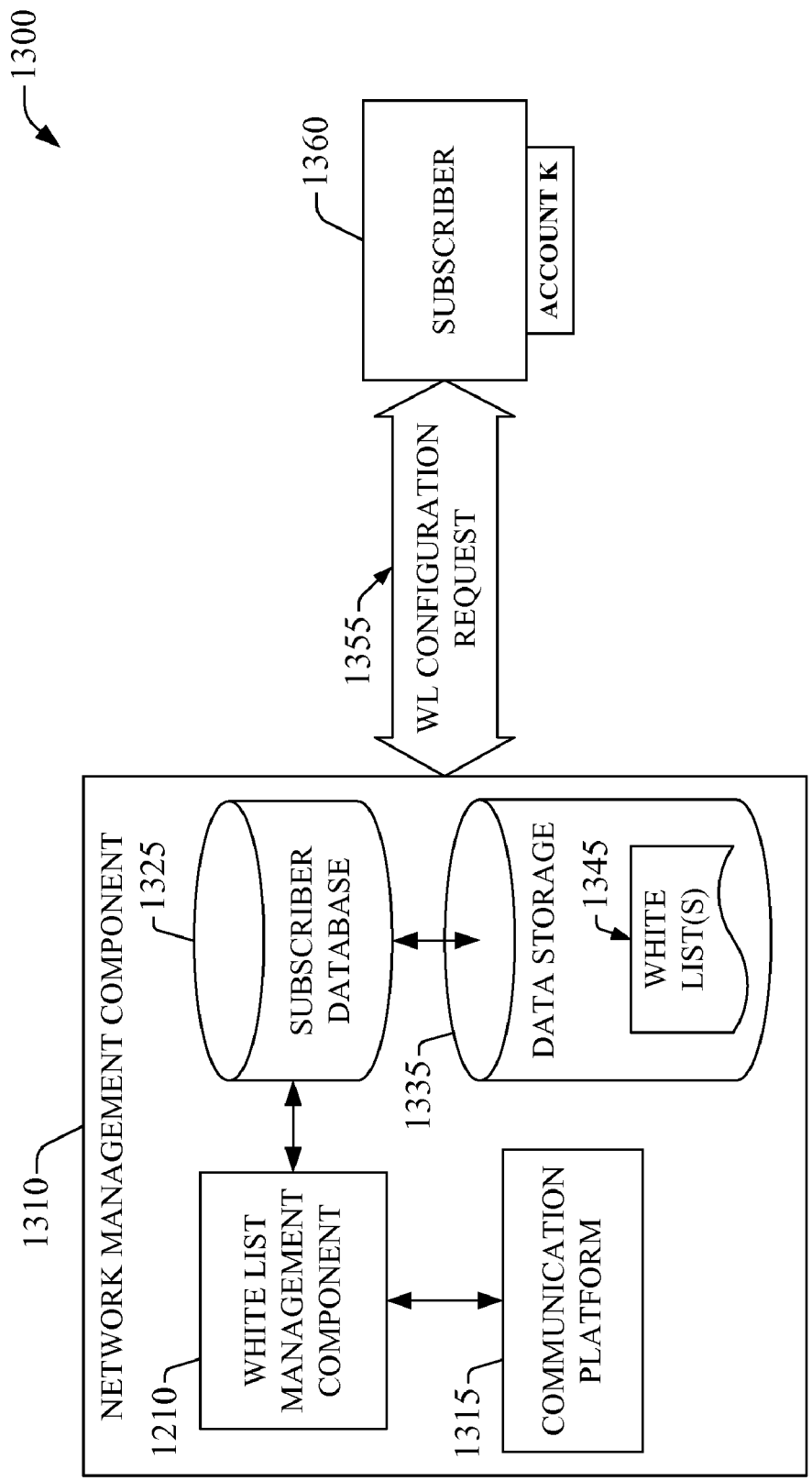
FIG. 13 is a block diagram of an example system that facilitates addition of subscriber(s)/subscriber station(s) to one or more white lists in accordance with aspects described in the subject specification.

FIG. 13 is a block diagram of an example system 1300 that facilitates addition of subscriber(s)/subscriber station(s) to one or more white list(s) 1345. In example system 1300, a network management component 1310 (e.g., a provisioning server) includes a white list management component 1210 which is coupled to a subscriber database 1325, a data storage 1335 and a communication platform 1315. The white list management component 1210 can data-mine, e.g., through a data mining component 351, subscriber database 1325 and white list(s) 1345, which resides in data storage 1335, to drive addition of new subscribers who have opted in to be included in white list(s) to a white list to request reciprocal adding. In an aspect, when a subscriber 1360 in account K is identified for reciprocal addition, at a time the subscriber 1360 configures his/her femto AP, a white list (WL) configuration request 1355 is conveyed (e.g., via a wired or wireless link through communication platform 1315) to the subscriber. Such WL configuration request 1355 indicates that a disparate subscriber (e.g., subscriber B 1130) has subscriber 1360 whitelisted and prompts subscriber 1360 to include in his/her white list the disparate subscriber. An illustrative scenario is the following: User 1 adds User 2 to his/her white list. Once User 2 configures/activates his/her femto cell, a setup process (implemented, for example, through a web-based online GUI) will prompt User 2 to add User 1. It is to be noted that white list management component 1210 can exploit information in subscriber database 1325 and data storage 1335 to inform User 2 of substantially all subscriber station numbers, codes or tokens that he/she can add automatically on a reciprocity basis; namely, User 2 can be prompted to add in white list(s) those subscribers that have previously added him/her to their with list(s). White list configuration request 1355 can be effected through various interfaces like an online GUI, a real time prompt/alert delivered via SMS, MMS, email, instant message (IM), and so forth.

Figure 14:
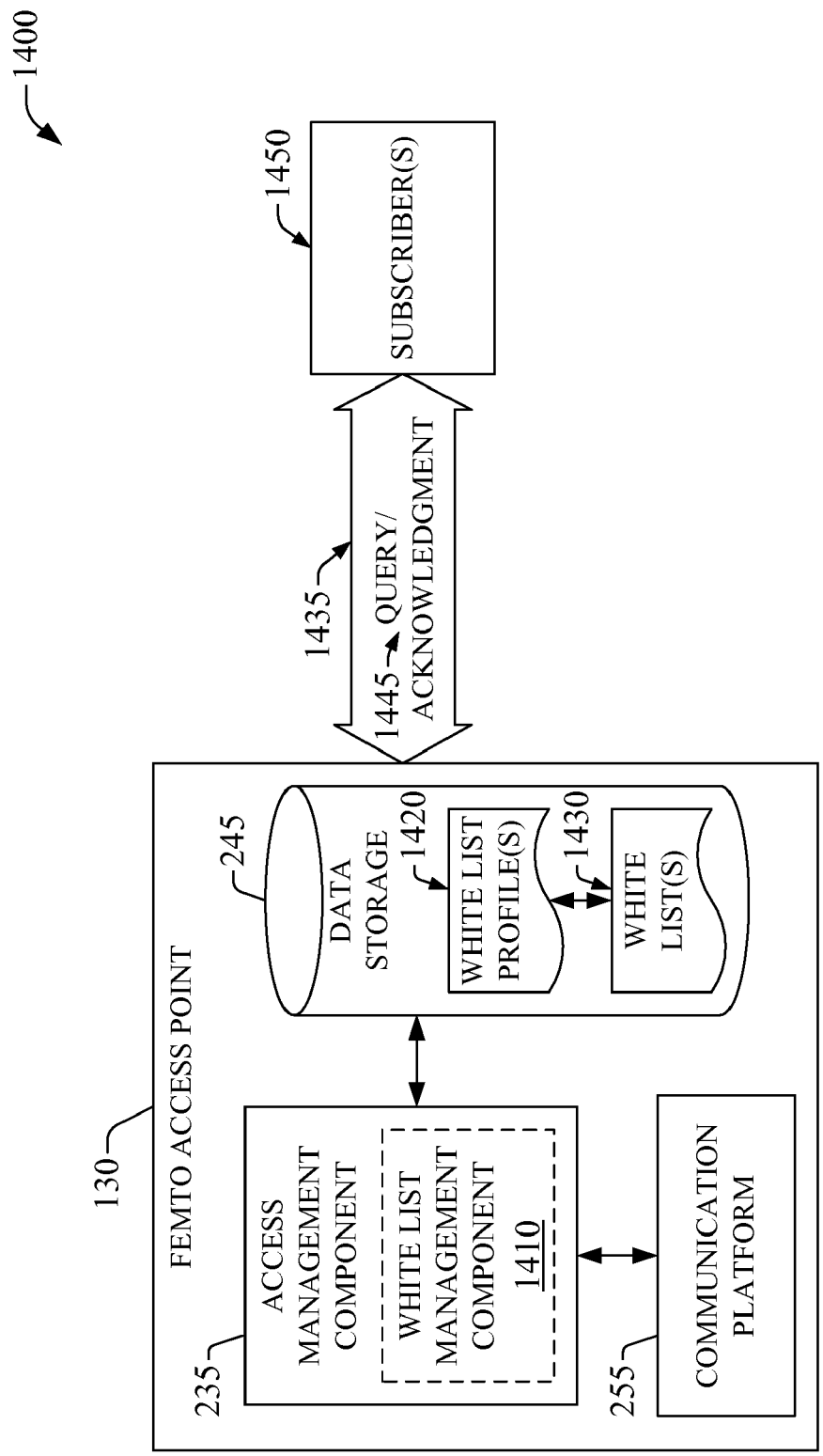
FIG. 14 is a block diagram of an example system that manages a defined logic of how content(s) in access control list(s), or white list(s), is maintained on a white list database in accordance with aspects described herein.

FIG. 14 is a block diagram of an example system 1400 that manages a defined logic of how content(s) (e.g., MSISDNs, IMSIs, IMEIs . . . ) in access control list(s), or white list(s), is maintained on a white list database, which can be embodied in data storage 245. Access management component 235, which can comprise a white list management component 1410 which can operate in substantially the same manner as white list management component 347, can develop white list profile(s) 1420 that applies logic and parameters that control, or manage, content in white list(s) 1430 such as subscriber station numbers (e.g., MSISDNs, IMSIs, IMEIs . . . ), codes, or tokens. White list component 1410 can operate in substantially the same manner as white list component 347. White list profile(s) 1420 and white list(s) 1430 can be stored in data storage 1415; it should be appreciated that while data storage 1415 is illustrated to reside within femto access point 130, such storage can reside in a network management component (e.g., component 1310), or can be functionally coupled thereof.

In an aspect, white list profile(s) 1420 parameters that control utilization logic of white list(s) 1430 content include, without being limited to including: (i) temporary access, e.g., full access for a specific time interval such as days or hours; (ii) access only within a window of time in a day (voice and data allowed from 9:00 a-6:00 p, or voice allowed after 9:00 p which can facilitate billing schemes already established by an operator/service provider); (iii) access to specific applications such as scheduler, calendar(s), news streaming, authoring tools, gaming, video and music, etc; (iv) access to femto AP 130 coverage with specific QoS profile(s), band width, allocated power for communication, or when specific conditions are met such as a specific available capacity . . . . As discussed above in connection with example system 300, white list profile(s) 1420 can be automatically populated based upon inferences drawn from historic operational data, e.g., call activity, associated with a set of identifiers (e.g., MSIDNSs, IMSIs, ESNs . . . ) that populate a white list(s) 1430.

In another aspect, as indicate above, logic within white list profile(s) 1420 can implement parameters to determine how long access to femto coverage is granted. For instance, when a timer associated with temporary access expires, a query 1445 can be triggered or conveyed (e.g., through a wired or wireless link 1435) to either a subscriber that operates a device associated with the managed identifier (e.g., MSISDN) in order to prompt or request renewed access, or to a subscriber that operates femto access point 130. The message request, e.g., query 1445, can prompt the subscriber that owns femto AP 130 whether an extension is to be granted or not. When a request is not granted by a subscriber that operates femto AP 130 or there is no reply, e.g., acknowledgement (ACK) 1447, from the subscriber owner, access to femto coverage expires and the identifier (e.g., MSISDN, or substantially any identifier code or token) linked to an identified mobile device is deleted from a corresponding white list(s) 1430 within data storage 245. It should be appreciated that the deletion can be "soft," e.g., the identifier is flagged as inactive, or "hard," wherein the identifier is deleted and a field or slot in a white list(s) 1420 is made available. Conversely, a positive response, e.g., acknowledgement 1445, from subscriber owner can allow access to continue based on either parameters extant in white list profile(s) 1420, or newly defined or negotiated access logic parameters. It is to be noted that query 1445 can be conveyed via an online GUI, an email message, a SMS message, MMS message, a voice mail, a web prompt, and the like.

Figure 15:
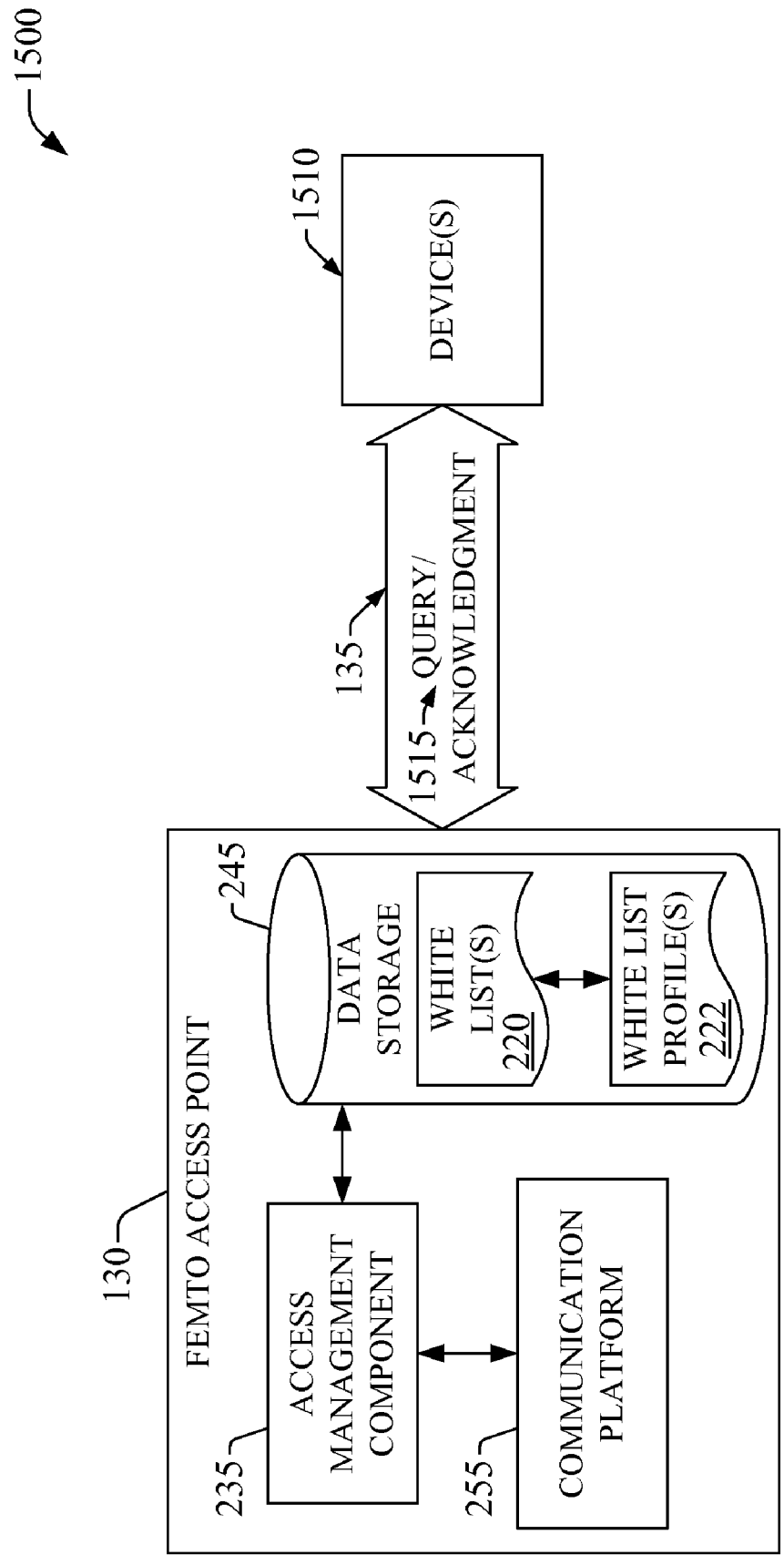
FIG. 15 is a block diagram of an example system that facilitates addition to a white list of mobile devices on an ad hoc basis in accordance with aspects described herein.

FIG. 15 is a block diagram of an example system 1500 that facilitates addition to a white list of mobile devices on an ad hoc basis in accordance with aspects described herein. In example system 1500, device(s) 1510 can convey a request or query 1515 to access coverage of femto AP 130; query 1515 can be delivered in a control channel when femto AP 130 operates in wireless broadband mode or in a management frame or packet when inband operation of femto AP 130 is implemented. It should be appreciated that a multi-mode chipset can operate, at least in part, communication platform 255 in order for it to receive and convey signal in various telecommunication mode(s). Query 1515 can be received by communication platform 255, and access management component 235 can be configured to allow or reject the request; allowance of rejection of a request can be based on various metrics, such as security, type of device, profile of subscriber that operated the device that requests access, and so on. Upon allowance of a request, access management component 235 can query for available slots, or fields, to be filled in white list(s) 220 associated with accounts served by femto AP 130, when space is available for a subscriber station identifier number (e.g., MSISDN, IMSI, ESN, IMEI), code or token, the query can further probe whether access is allowed on a permanent, or temporary basis (e.g., to reduce risk exposure to security problems). Characteristics of femto coverage allowance can be set or pre-set through access management component 235 via a determination of white list(s) 220 and associated white list profile(s) 222. Subsequent to allowance and examination of information related to relevant white list(s) 220, access management component 235 updates white list(s) 220, and related white list profile(s) 222, stored in data storage 245, to reflect the approved request for femto coverage. Upon an identifier for device 1510 is entered in white list 220, an acknowledgment (ACK) 1517 is delivered to device 1510 to indicate addition to the white list(s) 220 and femto service privileges accorded via white list profile(s) 222. It is to be noted that access and update of collected subscriber identifier numbers (e.g., MSISDN, IMSI), codes, or tokens, can also be effected through network-based white list database(s). It is to be noted that query 1515 can be conveyed via an online GUI, an email message, a SMS message, MMS message, a voice mail, a web prompt, USSD (or * and # codes) messaging, and the like.

An illustrative, non-limiting advantage of example system 1500 is that it provides an enhanced end user experience with a direct, clear mechanism to add new mobile device identifiers in white list, and thus encourages use of the femto access point 130, and avoids time spent on edition of white list(s) through a networked interface (e.g., interface component 210) like an online interface which takes time, a minimum degree of technological savvy, for the end user to access to the Internet and log on in a secured interface.

It should be appreciated that substantially any wireless device within coverage area of femto AP 130 (e.g., area 125) can request access without intervention of a subscriber that operates femto AP 130, and who has previously entered a set of subscriber station numbers (e.g., MSISDNs), codes or tokens, via a networked interface (e.g., interface component 210). Alternatively, or in addition, a request for access can be prompted by a device utilized by a subscriber that operates the femto AP. Further a request for access can be effected by the femto AP, through an access management component like component 235, for example. Once a request is granted, a secure tunnel can be established from the device/client through the femto cell's IP connection or the default of the Radio Access Network if the IP connection is not available. Secure layers including utilizing the femto cell's VPN and/or USSD would ensure that the transaction related to edition or manipulation of a white list is in fact secure. As a non-limiting example, a temporary visitor or employee (e.g., a babysitter) who is coming over to a location served by a femto access point (e.g., femto AP 130) for a limited period of time, can be provided with coverage via the femto AP by a subscriber that operates the femto cell so the employee can perform, at least in part, his work activities (e.g., provide updates on behavior of children, be contacted reliably through a mobile device . . . ) through utilization of the femto access point. In case the subscriber fails to know identifier numbers (e.g., MSISDNs, IMSIs), codes, or tokens for mobile devices the employee can utilize, and the subscriber is not interested to go through the process of requesting and entering the numbers (e.g., MSISDNs, IMSIs), codes or tokens via a networked interface to allow coverage for the limited period of time the employee performs work, the employee (e.g., babysitter) can convey a request (e.g., query 1515) for access to femto coverage directly from the employee's device when in range of the femto access point (e.g., within area 125).

Figure 16:
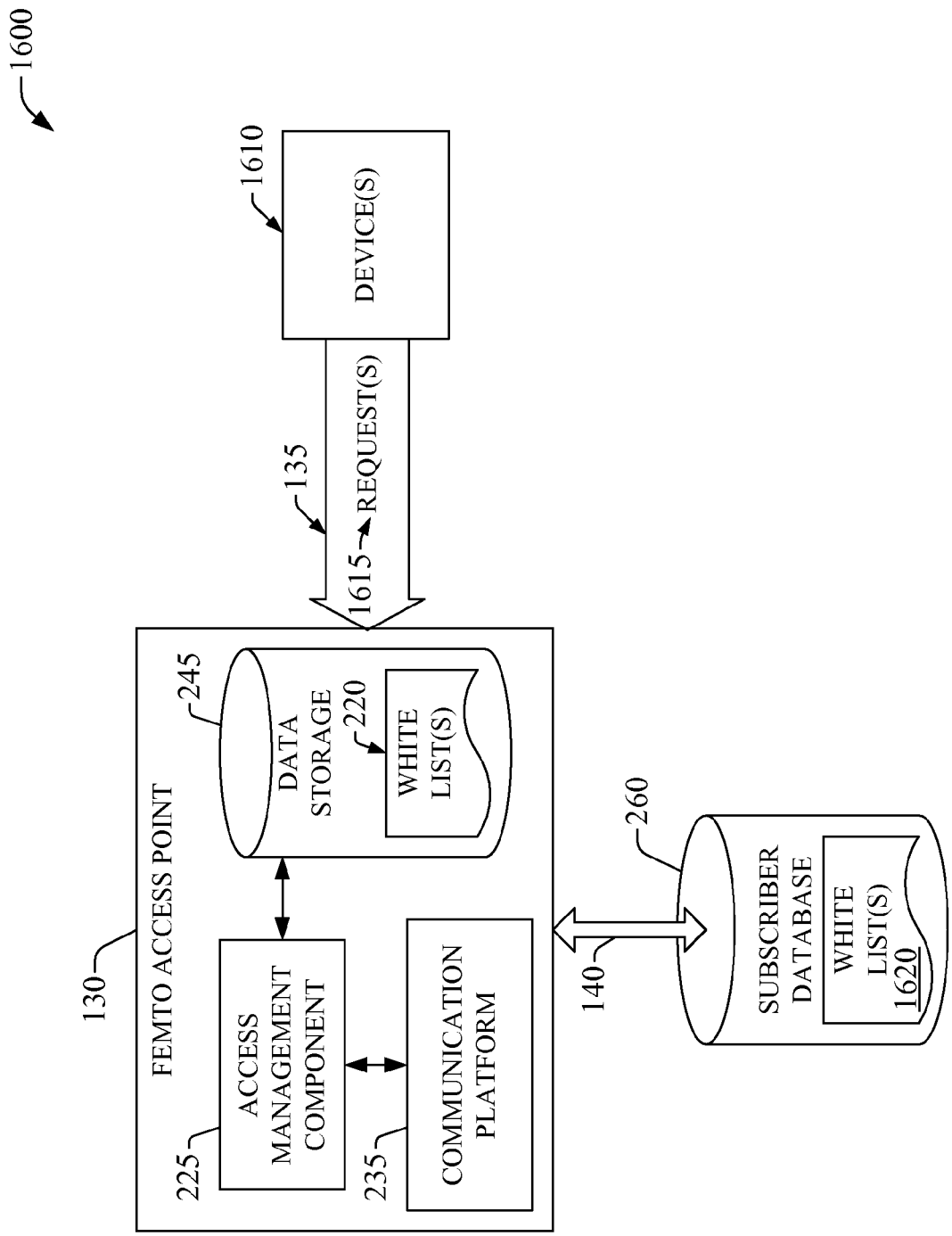
FIG. 16 is a block diagram of an example system that tracks subscriber station identifier numbers (e.g., MSISDNs), codes or tokens, associated with white list(s) on record with a femto service provider in accordance with aspects of the subject innovation.

FIG. 16 is a block diagram of an example system 1600 that tracks subscriber station identifier numbers (e.g., MSISDNs, IMSIs), codes or tokens, associated with white list(s) on record with a femto service provider in accordance with aspects of the subject innovation. When a subscriber (e.g., subscriber A 1110), or end user, that operates mobile device(s) 1610 cancels an account or subscription with a service provider or changes identifier number, code, or token associated with mobile device(s) 1610, the subscriber can convey a request 1615 via mobile device(s) 1610 to remove the identifier number thereof from substantially all, or all, white list(s) 1620 on record in a subscriber database 260 or substantially any other database available to a service provider that contains information on service subscribers. In an aspect, access management component 225 can convey an indication, via backhaul pipe 140, to update white lists to a mobile wireless platform (e.g., a core network) in accordance to request(s) 1615. It is noted that local records of white list(s) 220 are also updated; local update takes place in all femto APs that include white list(s) that comprise mobile device 1610 identifier number that is cancelled.

Additionally, or alternatively, when an end user changes his/her mobile or subscriber station number, code or token, (e.g., after relocation to a new area code, or the like), request(s) 1615 can be delivered to femto access point 130 to automatically update substantially all, or all, white list(s) 1620 on record that include mobile device 1610 identifier number, code, or token. Access management component 225 can deliver signaling via backhaul pipe 140 to a mobile network platform to update white list(s) 1620 records in subscriber database 260. It is noted that local records of white list(s) 220 are also updated.

An illustrative advantage of such on-request automatic update of white list(s) 1620, and local white list(s) 220, is ease of use for end users to maintain current white lists at the network level and local, e.g., femto AP 130, level without a need to track each subscriber station number, code, or token associated with the white list(s) 1620. In addition, updated white list(s) 1620 and white list(s) 220 maintain the value proposition of the femto cells for end users and service operator by a seamless move of traffic off of the macro network (e.g., a WAN) to femto network(s).

Figure 17:
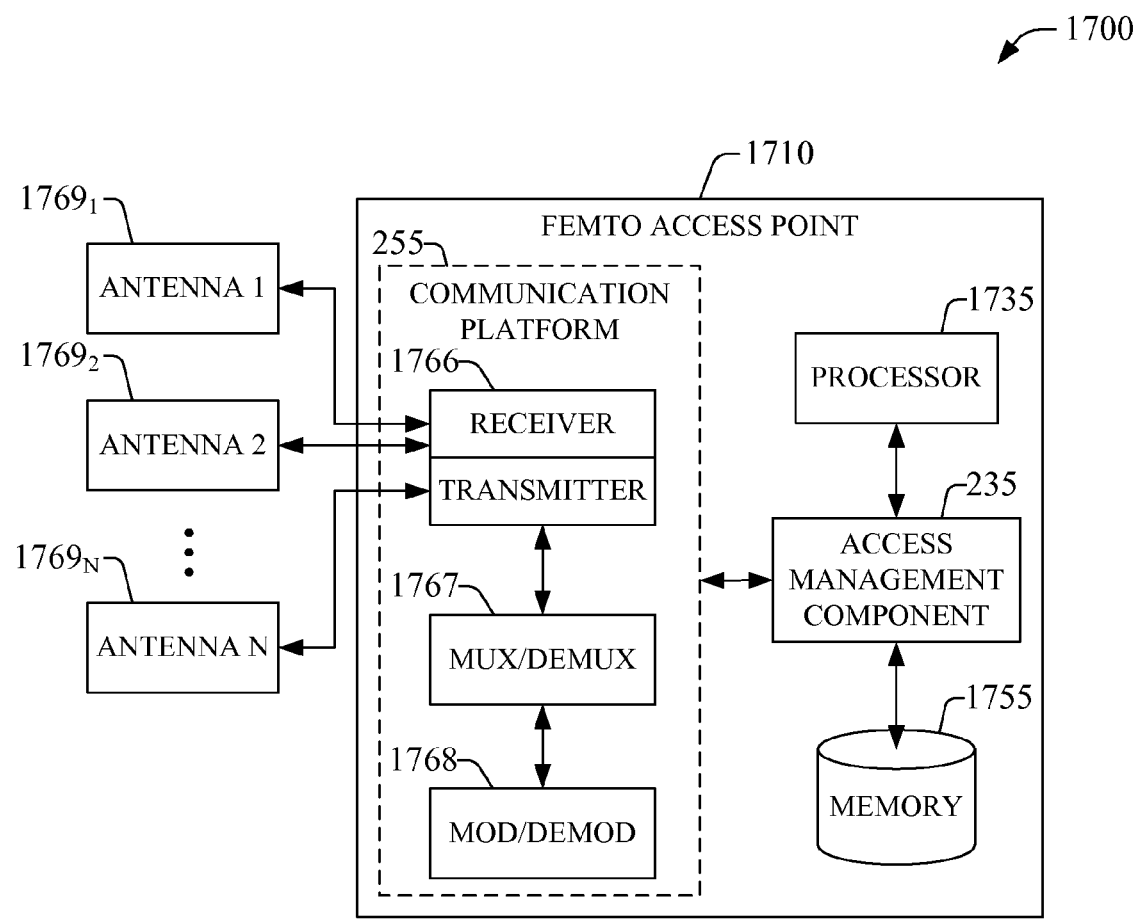
FIG. 17 is a block diagram of an example femto access point that operates in accordance with aspects disclosed in the subject specification.
Figure 18:
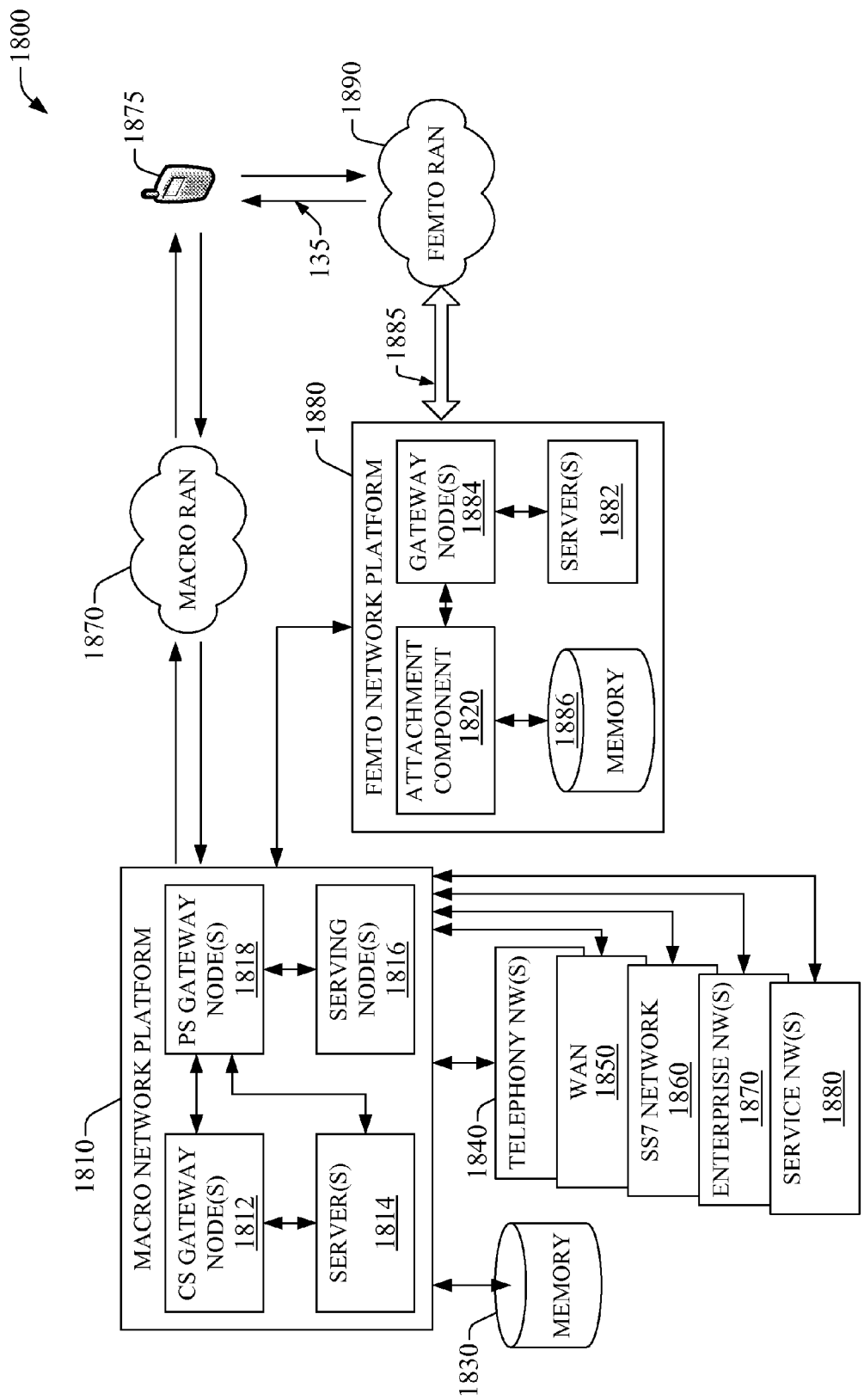
FIG. 18 illustrates example macro and femto wireless network environments that can enable and implement various aspects of the subject innovation, and can exploit femto APs that operate according to the various aspects.

To provide further context for various aspects or features of the subject specification, in system in which aspects or features of the subject innovation can be exploited, FIG. 17 illustrates a block diagram of an example embodiment 1700 of a femto access point that can enable and exploit and manage femto coverage via access control list(s), or white list(s), in accordance with aspects described herein. In addition, FIG. 18 illustrates a block diagram of an illustrative telecommunication network 1800 that can enable, or implement, and exploit features and aspects described herein. Those skilled in the art will recognize that the specification also be implemented through program modules stored in a memory and executed by a processor, and/or other combination of hardware and software.

With respect to FIG. 17, in embodiment 1700, femto AP 1710 can receive and transmit signal(s) from and to wireless devices like macro and femto access points, access terminals, wireless ports and routers, and the like, through a set of antennas $1769_1$-$1769_N$. It should be appreciated that while antennas $1769_1$-$1769_N$ are a part of communication platform 255, which comprises electronic components and associated circuitry that provides for processing and manipulation of received signal(s) and signal(s) to be transmitted. In an aspect, communication platform 255 includes a receiver/transmitter 1766 that can convert signal from analog to digital upon reception, and from digital to analog upon transmission. In addition, receiver/transmitter 1766 can divide a single data stream into multiple, parallel data streams, or perform the reciprocal operation. Coupled to receiver/transmitter 1766 is a multiplexer/demultiplexer 1767 that facilitates manipulation of signal in time and frequency space. Electronic component 1767 can multiplex information (data/traffic and control/signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 1767 can scramble and spread information (e.g., codes) according to substantially any code known in the art; e.g., Hadamard-Walsh codes, Baker codes, Kasami codes, polyphase codes, and so on. A modulator/demodulator 1768 is also a part of operational group 1725, and can modulate information according to multiple modulation techniques, such as frequency modulation, amplitude modulation (e.g., M-ary quadrature amplitude modulation (QAM), with M a positive integer), phase-shift keying (PSK), and the like.

Femto access point 1710 also includes a processor 1735 configured to confer functionality, at least partially, to substantially any electronic component in the femto access point 1710. In particular, processor 1735 can facilitate access management component 235 to operate in accordance to aspects disclosed herein. In addition, processor 1735 can facilitate operations on data (e.g., symbols, bits, or chips) for multiplexing/demultiplexing, such as effecting direct and inverse fast Fourier transforms, selection of modulation rates, selection of data packet formats, inter-packet times, etc. A memory 1755 can store data structures, code instructions, system or device information like policies and specifications, code sequences for scrambling, spreading and pilot transmission, floor plan configuration, access point deployment and frequency plans, scheduling policies, and so on.

In embodiment 1700, processor 1734 is coupled to the memory 1755 in order to store and retrieve information necessary to operate and/or confer functionality to communication platform 255, access management component 235, and other operational aspects of femto access point 1710.

With respect to FIG. 18, wireless communication environment 1800 includes two wireless network platforms: (i) A macro network platform 1810 which serves, or facilitates communication with user equipment 1875 (e.g., mobile 120$_A$) via a macro radio access network (RAN) 1870. It should be appreciated that in cellular wireless technologies (e.g., 3GPP UMTS, HSPA, 3GPP LTE, 3GPP2 UMB), macro network platform 1810 is embodied in a Core Network. (ii) A femto network platform 1880, which can provide communication with UE 1875 through a femto RAN 1890, which is linked to the femto network platform 1880 via backhaul pipe(s) 1885 (e.g., backhaul link(s) 140). It should be appreciated that macro network platform 1810 typically hands off UE 1875 to femto network platform 1810 when UE 1875 attaches (e.g., through macro-to-femto handover) to femto RAN 1890, which includes a set of deployed femto APs (e.g., femto AP 130) that can operate in accordance with aspects described herein.

It is noted that RAN includes base station(s), or access point(s), and its associated electronic circuitry and deployment site(s), in addition to a wireless radio link operated in accordance with the base station(s). Accordingly, macro RAN 1870 can comprise various coverage cells like cell 105, while femto RAN 1890 can comprise multiple femto cell access points such as femto AP 130. Deployment density in femto RAN 1890 is substantially higher than in macro RAN 1870.

Generally, both macro and femto network platforms 1810 and 1880 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject innovation, macro network platform 1810 includes CS gateway node(s) 1812 which can interface CS traffic received from legacy networks like telephony network(s) 1840 (e.g., public switched telephone network (PSTN), or public land mobile network (PLMN)) or a SS7 network 1860. Circuit switched gateway 1812 can authorize and authenticate traffic (e.g., voice) arising from such networks. Additionally, CS gateway 1812 can access mobility, or roaming, data generated through SS7 network 1860; for instance, mobility data stored in a VLR, which can reside in memory 1830. Moreover, CS gateway node(s) 1812 interfaces CS-based traffic and signaling and gateway node(s) 1818. As an example, in a 3GPP UMTS network, PS gateway node(s) 1818 can be embodied in gateway GPRS support node(s) (GGSN).

In addition to receiving and processing CS-switched traffic and signaling, PS gateway node(s) 1818 can authorize and authenticate PS-based data sessions with served (e.g., through macro RAN) wireless devices. Data sessions can include traffic exchange with networks external to the macro network platform 1810, like wide area network(s) (WANs) 1850, enterprise networks (NW(s)) 1870 (e.g., enhanced 911), or service NW(s) 1880 like IP multimedia subsystem (IMS); it should be appreciated that local area network(s) (LANs), which may be a part of enterprise NW(s), can also be interfaced with macro network platform 1810 through PS gateway node(s) 1818. Packet-switched gateway node(s) 18 generates packet data contexts when a data session is established. To that end, in an aspect, PS gateway node(s) 1818 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 1814. It is to be noted that in 3GPP UMTS network(s), PS gateway node(s) 1818 (e.g., GGSN) and tunnel interface (e.g., TTG) comprise a packet data gateway (PDG).

Macro network platform 1810 also includes serving node(s) 1816 that convey the various packetized flows of information, or data streams, received through PS gateway node(s) 1818. As an example, in a 3GPP UMTS network, serving node(s) can be embodied in serving GPRS support node(s) (SGSN).

As indicated above, server(s) 1814 in macro network platform 1810 can execute numerous applications (e.g., location services, online gaming, wireless banking, wireless device management . . . ) that generate multiple disparate packetized data streams or flows, and manage (e.g., schedule, queue, format . . . ) such flows. Such application(s), for example can include add-on features to standard services provided by macro network platform 1810. Data streams can be conveyed to PS gateway node(s) 1818 for authorization/authentication and initiation of a data session, and to serving node(s) 1816 for communication thereafter. Server(s) 1814 can also effect security (e.g., implement one or more firewalls) of macro network platform 1810 to ensure network's operation and data integrity in addition to authorization and authentication procedures that CS gateway node(s) 1812 and PS gateway node(s) 1818 can enact. Moreover, server(s) 1814 can provision services from external network(s), e.g., WAN 1850, or Global Positioning System (GPS) network(s), which can be a part of enterprise NW(s) 1880. Furthermore, one or more of server(s) 1814 can embody provisioning server 345 and components therein, with functionality described hereinbefore. It is to be noted that server(s) 1814 can include one or more processor configured to confer at least in part the functionality of macro network platform 1810. To that end, the one or more processor can execute code instructions stored in memory 1830, for example.

In example wireless environment 1800, memory 1830 stores information related to operation of macro network platform 1810. Information can include business data associated with subscribers; market plans and strategies, e.g., promotional campaigns, business partnerships; operational data for mobile devices served through macro network platform; service and privacy policies; end-user service logs for law enforcement; and so forth. Memory 1830 can also store information from at least one of telephony network(s) 1840, WAN 1850, SS7 network 1860, enterprise NW(s) 1870, or service NW(s) 1880.

Regarding femto network platform 1880, it includes a femto gateway node(s) 1884, which have substantially the same functionality as PS gateway node(s) 1818. Additionally, femto gateway node(s) 1884 can also include substantially all functionality of serving node(s) 1816. Disparate gateway node(s) 1884 can control or operate disparate sets of deployed femto APs, which can be a part of femto RAN 1890. In an aspect of the subject innovation, femto gateway node(s) 1884 can aggregate operational data received from deployed femto APs. Moreover, femto gateway node(s) 1884, can convey received attachment signaling to attachment component 1820. It should be appreciated that while attachment component is illustrated as external to gateway node(s) 1884, attachment component 1820 can be an integral part of gateway node(s) 1884.

Attachment component 1820 can facilitate macro-to-femto and femto-to-macro handover with attachment to a femto AP (e.g., femto AP 130) dictated in accordance to a white list (e.g., white list(s) 220) and/or a white list profile (e.g., white list profile(s) 222). In an aspect, attachment component 1820 can include a determination of whether a white list resides within femto AP and whether a mobile station that is attempting attachment is whitelisted as described in the subject innovation. It is noted, in an aspect, that when a whitelisted mobile station is allowed to attach to the femto AP, attachment component 1820 can establish femto service in accordance with privileges, or access logic, configured in a white list profile (e.g., white list profile(s) 222).

Memory 1886 can retain additional information relevant to operation of the various components of femto network platform 1880. For example operational information that can be stored in memory 1886 can comprise, but is not limited to, subscriber intelligence; contracted services; maintenance and service records; femto cell configuration (e.g., devices served through femto RAN 1890; authorized subscribers associated with one or more deployed femto APs); service policies and specifications; privacy policies; add-on features; so forth.

Server(s) 1882 have substantially the same functionality as described in connection with server(s) 1814. In an aspect, server(s) 1882 can execute multiple application(s) that provide service (e.g., voice and data) to wireless devices served through femto RAN 1890. Server(s) 1882 can also provide security features to femto network platform. In addition, server(s) 1882 can manage (e.g., schedule, queue, format . . . ) substantially all packetized flows (e.g., IP-based, frame relay-based, ATM-based) it generates in addition to data received from macro network platform 1810. Furthermore, server(s) 1882 can effect provisioning of femto cell service, and effect operations and maintenance. It is to be noted that server(s) 1882 can embody provisioning server 345, and can populate white list(s) and white list profile(s) in accordance with aspects described herein. It is to be noted that server(s) 1882 can include one or more processors configured to provide at least in part the functionality of femto network platform 1880. To that end, the one or more processors can execute code instructions stored in memory 1886, for example.

Various aspects or features described herein may be implemented as a method, apparatus, or article of manufacture using standard programming and/or engineering techniques. Implementation(s) that include software or firmware can be implemented at least in part through program modules stored in a memory and executed by a processor. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disc (CD), digital versatile disc (DVD), blu-ray disc (BD) . . . ), smart cards, and flash memory devices (e.g., card, stick, key drive . . . ).

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," data storage," "database," and substantially any other information storage component relevant to operation and functionality of a component, refer to "memory components," or entities embodied in a "memory" or components comprising the memory. For example, information relevant to operation of various components described in the disclosed subject matter, and that can be stored in a memory, can comprise, but is not limited to comprising, subscriber information; femto cell configuration (e.g., devices served by a femto AP; access control lists, or white lists) or service policies and specifications; privacy policies; and so forth. It will be appreciated that the memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

What has been described above includes examples of systems and methods that provide advantages of the subject innovation. It is, of course, not possible to describe every conceivable combination of components or methodologies for purposes of describing the claimed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A method comprising:
   receiving, by a system comprising at least one processor, data related to subscriber call activity associated with a femtocell;
   determining, by the system, a set of respective identifiers for a set of mobile devices authorized to connect to the femtocell, based on analyzing the data, wherein the determining includes inferring the set of respective identifiers based at least in part on detecting a pattern within the subscriber call activity;
   identifying, by the system, an out-of-network phone number based on the pattern;
   requesting, by the system, a device associated with the out-of-network phone number to elect to be added within a white list of the femtocell via a text message; and
   adding, by the system, a subset of the set of respective identifiers to the white list of the femtocell.

2. The method of claim 1, further comprising:
   selecting, by the system, the subset of the set of respective identifiers based in part on a cut-off procedure; and validating, by the system, the subset of the set of respective identifiers prior to the adding.

3. The method of claim 2, wherein the validating includes verifying that a subset of the set of mobile devices corresponding to the subset of the set of respective identifiers has opted for inclusion within the white list.

4. The method of claim 2, wherein the validating includes verifying a commercial standing of a subset of the set of mobile devices corresponding to the subset of the set of respective identifiers.

5. The method of claim 1, further comprising: generating, by the system, a white list profile for managing content within the white list based on a set of subscriber-defined coverage parameters.

6. The method of claim 5, wherein the generating includes generating a default white list profile that allows a subset of the set of mobile devices corresponding to the subset of the set of respective identifiers full access to femto coverage.

7. The method of claim 1, further comprising: transmitting, by the system, the white list to a provisioned access point associated with the femtocell.

8. The method of claim 1, wherein the receiving includes extracting the data from a set of databases.

9. The method of claim 8, further comprising: identifying, by the system, an in-network phone number based on the pattern.

10. The method of claim 1, wherein the adding includes adding the out-of-network phone number to the white list of the femtocell in response to receiving an election from the device approving the adding the out-of-network phone number to the white list.

11. The method of claim 1, wherein the receiving includes collecting data from an address book associated with a user equipment of the subscriber.

12. A system, comprising:
at least one memory;
at least one processor communicatively coupled to the at least one memory that facilitates execution of at least one computer-executable component to at least:
collect data related to call activity of a user equipment associated with a subscriber of a femtocell;
determine a set of respective identifiers for a set of mobile devices based on an analysis of the data including infer the set of respective identifiers based at least in part on detection of a pattern within the call activity, wherein the set of respective identifiers includes an out-of-network phone number that is identified based on the pattern;
request a device associated with the out-of-network phone number to elect to be added within a white list of the femtocell via a text message; and
populate the white list of the femtocell with a subset of the set of respective identifiers.

13. The system of claim 12, wherein the at least one processor further facilitates the execution of the at least one computer-executable component to validate the subset of the set of respective identifiers based at least in part on a predefined criterion, prior to including the subset of the set of respective identifiers in the white list.

14. The system of claim 13, wherein the criterion includes an election by a subset of the set of mobile devices corresponding to the subset of the set of respective identifiers to be included within the white list.

15. The system of claim 13, wherein the criterion includes an operational capability associated with a mobile device related to one of the set of respective identifiers.

16. The system of claim 13, wherein the criterion includes a commercial standing associated with a mobile device related to one of the set of respective identifiers.

17. The system of claim 12, wherein the at least one processor further facilitates the execution of the at least one computer-executable component to extract information from a subscriber database within a communication network and infer the set of respective identifiers based on the information.

18. The system of claim 12, wherein the data includes data that is received from an address book of the user equipment.

19. The system of claim 12, wherein the at least one processor further facilitates the execution of the at least one computer-executable component to collect information associated with the set of mobile devices to generate a set of coverage parameters to be entered in a white list profile associated with the white list.

20. The system of claim 12, wherein the at least one processor further facilitates the execution of the at least one computer-executable component to receive a set of coverage parameters via a user interface.

21. The system of claim 13, wherein the at least one processor further facilitates the execution of the at least one computer-executable component to populate a white list profile associated with the white list, wherein the white list profile determines logic for the set of mobile devices to access femto coverage.

22. A non-transitory computer-readable medium comprising computer-executable instructions that, in response to execution, cause a system comprising at least one processor to perform operations comprising:
receiving data related to call activity of a communication device related to a subscriber of a femtocell;
determining an identifier related to a mobile device authorized to connect to the femtocell based on the data, wherein the determining includes inferring an out-of-network phone number associated with the mobile device based at least in part on detecting a pattern within the call activity;
requesting the mobile device to elect to be added within a white list of the femtocell via a text message; and
including the identifier within the white list of the femtocell in response to the mobile device electing to be added within the white list.

* * * * *